United States Patent [19]

Ghosh et al.

[11] Patent Number: 5,478,893
[45] Date of Patent: Dec. 26, 1995

[54] END-ATTACHMENT OF OLIGONUCLEOTIDES TO POLYACRYLAMIDE SOLID SUPPORTS FOR CAPTURE AND DETECTION OF NUCLEIC ACIDS

[75] Inventors: Soumitra S. Ghosh; Eoin D. Fahy, both of San Diego, Calif.

[73] Assignee: Siska Diagnostics Inc., La Jolla, Calif.

[21] Appl. No.: 102,474

[22] Filed: Aug. 5, 1993

Related U.S. Application Data

[63] Continuation-in-part of Ser. No. 293,893, Jan. 5, 1989, Pat. No. 5,237,016.
[51] Int. Cl.$^6$ .................. C08F 120/56; C07H 21/02; C07H 21/04
[52] U.S. Cl. .................. 525/329.4; 536/25.3; 536/25.4; 536/23.1
[58] Field of Search .................. 435/6; 536/25.3, 536/25.4, 23.1; 525/329.4

[56] References Cited

U.S. PATENT DOCUMENTS

| | | | |
|---|---|---|---|
| 4,486,539 | 12/1984 | Ranki et al. | 436/504 |
| 4,563,419 | 1/1986 | Ranki et al. | 435/6 |
| 4,581,333 | 4/1986 | Kourilsky et al. | 435/6 |
| 4,775,619 | 10/1988 | Urdea | 435/6 |
| 4,806,546 | 2/1989 | Carrico et al. | 536/25.3 |
| 4,806,631 | 2/1989 | Carrico et al. | 536/25.3 |
| 4,822,747 | 4/1989 | Johnson et al. | 436/532 |
| 4,898,824 | 2/1990 | Yip | 435/180 |

FOREIGN PATENT DOCUMENTS

| | | | |
|---|---|---|---|
| 0296557 | 12/1988 | European Pat. Off. | C12Q 1/68 |
| 3515529 | 11/1986 | Germany | C07H 21/00 |
| 8801302 | 2/1988 | WIPO | C12Q 1/68 |
| 8810315 | 12/1988 | WIPO | C12Q 1/68 |
| 9007582 | 7/1990 | WIPO | C12Q 1/68 |
| 9208808 | 5/1992 | WIPO | C12Q 1/68 |

OTHER PUBLICATIONS

"Handbook of Chem. & Phys.", Hodgman et al, eds. p. 1757 only, 1962 Chemical Rubber Publishing Co., Cleveland, Ohio.
March (1968) "Advanced Organic Chem.: Reactions, Mechanisms, & Structures", McGraw–Hill, Inc. p. 294 only.
Beck et al., "Chemiluminescent detection of DNA: application for DNA sequencing and hybridization," Nucleic Acids Res. 17(13):5115–5123 (1989).
Bernatowicz and Matsueda, "Preparation of peptide–protein immunogens using N–succinimidyl bromoacetate as a heterobifunctional crosslinking reagent," Analyt. Biochem. 155:95–102 (1986).
Bio–Rad Laboratories Catalog pp. 39–50 (1981).
Bischoff et al., "Introduction of 5'–terminal functional groups into synthetic oligonucleotides for selective immobilization," Anal. Biochem. 164:336–344 (1987).
Blanks and McLaughlin, "An oligodeoxynucleotide affinity column for the isolation of sequence specific DNA binding proteins," Nuc. Acids Res. 16(21):10283–10299 (1988).
Bronstein et al., "Acomparison of chemiluminescent and colorimetric substrates in a Hepatitis B virus DNA hybridization assay," Anal. Biochem. 180:95–98 (1989).
Bunemann et al., "Immobilization of denatured DNA to macroporous supports: I. Efficiency of different coupling procedures," Nuc. Acids Res. 10(22):7163–7180 (1982).
Bunemann, H., "Immobilization of denatured DNA to macroporous supports: II. Steric and kinetic parameters of heterogenous hybridization reactions," Nuc. Acids Res. 10(22):7181–7196 (1982).
Chu and Orgel, "Ligation of oligonucleotides to nucleic acids aor proteins via disulfide bonds," Nuc. Acids Res. 16(9):3671–3691 (1988).
Chu et al., "Synthesis of an amplifiable reporter RNA for bioassays," Nuc. Acids Res. 14(14):5591–5603 (1986).
Chu et al., "Derivatization of unprotected polynucleotides," Nuc. Acids Res. 11(18):6513–6529 (1983).
Connolly, B., "Chemical synthesis of oligonucleotides containing a free sulphydryl group and subsequent attachment of thiol specific probes," Nuc. Acids Res. 13(12):4485–4502 (1985).
Cuatreacasas, P., "Protein purification by affinity chromatography," J. Bio. Chem. 245:3059–3066 (1970).
Davis et al., "Detection of Human Immunodeficiency Virus Type 1 in AIDS patients using amplification–mediated hybridization analyses: Reproducibility and quantitative limitations," J. Infect. Dis. 162:13–20 (1990).
Gaur et al., "A simple method for the introduction of thiol group at 5'–termini of oligodeoxynucleotides," Nuc. Acids Res. 17(11):4404 (1989).
Ghosh et al., "Synthesis of 5'–oligonucleotide hydrazide derivatives and their use in preparation of enzyme–nucleic acid hybridization probes," Anal. Bioch. 178:43–51 (1989).
Ghosh et al., "Use of maleimide–thiol coupling chemistry for efficient syntheses of oligonucleotide–enzyme conjugate hybridization probes," Biocon. Chem. 1(1):71–76 (1990).

(List continued on next page.)

Primary Examiner—Mindy B. Fleisher
Assistant Examiner—Nancy T. Vogel
Attorney, Agent, or Firm—Stephanie L. Seidman; Brown Martin Haller & McClain

[57] ABSTRACT

Methods for covalent attachment of oligonucleotides to solid supports such that substantially all of the oligonucleotides are attached via their 5'-ends are provided. The solid supports with attached oligonucleotides are produced. Thiol-oligonucleotides are attached to bromoacetyl-derivatized polyacrylamide supports, or conversely, bromoacetyl-oligonucleotides are immobilized on thiol-polyacrylamide supports. In a further aspect, bromoacetyl-derivatized oligonucleotides, and polyacrylamide supports with linked oligonucleotides produced by coupling bromoacetyl-derivatized oligonucleotides with thiol-derivatized polyacrylamide solid supports or by coupling thiol-derivatized oligonucleotides with bromoacetyl-derivatized polyacrylamide supports as well as methods for capture of nucleic acids by oligonucleotides attached to polyacrylamide solid supports, either by direct capture or in sandwich hybridization formats are provided.

22 Claims, 6 Drawing Sheets

OTHER PUBLICATIONS

Ghosh and Musso, "Covalent attachment of oligonucleotides to solid supports," *Nuc. Acids Res.* 15(13):5353–5372 (1987).

Gordon et al., "Topographical localization of the C–terminal region of the voltage–dependent sodium channel from *Electrophorus electricus* using antibodies raised against a synthetic peptide," *P.N.A.S.* 84:308–312 (1987).

Gingeras et al., "Use of self–sustained sequence replication amplification reaction to analyze and detect mutations in Zidovudine–resistant Human Immunodificiency Virus," *J. Infec. Dis.* 164:1066–1074 (1991).

Goodchild, J., "Conjugates of oligonucleotides and modified oligonucleotides: A review of their synthesis and properties," *Bioconj. Chem.* 1(3):165–186 (1990).

Inman, J., "Covalent linkage of functional groups, ligands, and proteins to polyacrylamide beads," *Meth. Enzym.* 34(partB):30–39 (1974).

Duncan et al., "A new reagent which may be used to introduce sulfhydryl groups into proteins and its use in the preparation of conjugates for immunoassay," *Anal. Bioch.* 132:68–73 (1983).

Keller and Rudinger, "Preparation and some properties of maleimido acids and maleoyl derivatives of peptides," *Helv. Chimica Acta* 58:531–541 (1975).

Kremsky et al., "Immobilization of DNA via oligonucleotides containing an aldehyde or carboxylic acid group at the 5' terminus," *Nuc. Acids Res.* 15(7):2891–2909 (1987).

Kwoh et al., "Transcription–based amplification system and detection of amplified human immunodeficiency virus type 1 with a bead–based sandwich hybridization format," *P.N.A.S.* 86:1173–1177 (1989).

Lambert et al., "Cross–links between ribosomal proteins of 30S subunits in 70S tight couples and in 30S subunits," *Biochem.* 22:3913–3920 (1983).

Lambert and Traut, "The subunit interface of the *Escherichia coli* ribosome," *J. Mol. Biol.* 149:451–476 (1981).

Langdale and Malcolm, "A rapid method of gene detection using DNA bound to Sephacryl," *Gene* 36:201–210 (1985).

Li et al., "Enzyme–linked synthetic oligonucleotide probes: non–radioactive detection of enterotoxigenic *E. coli* in faecal specimens," *Nuc. Acids Res.* 15(13):5275–5287 (1987).

Lund et al., "Assessment of methods for covalent binding of nucleic acids to magnetic beads, Dynabeads™, and the characteristics of the bound nucleic acids in hybridization reactions," *Nuc. Acids Res.* 16(22):10861–10881 (1988).

Mahan et al., "Phase change enzyme immunoassay," *Anal. Biochem.* 162:163–170 (1987).

Pongs and Lanka, "Synthesis of a chemically reactive analog of the initiation condon its reaction with ribosomes of *Escherichia coli*," *Hoppe Seyler's Z. Physiol. Chem.* 356:449–458 (1975).

Syvanen et al., "Quantification of polymerase chain reaction products by affinity–based hybrid collection," *Nuc. Acids Res.* 16(23):11327–11339 (1988).

Tanaka et al., "Synthesis of oligodeoxyribonucleotide with aliphatic amino or phosphate group at the 5' end by the phosphotriester method on a polysyrene support,".

Urdea et al., "A novel method for the rapid detection of specific nucleotide sequences in crude biological samples without blotting or radioactivity; application to the analysis of hepatitis B virus in human serum," *Gene* 61:253–264 (1987).

Voss and Malcolm, "The immobilization of oligonucleotides and their hybridization properties," *Biochem. Soc. Trans.* 16:216–217 (1988).

Wachter et al., "A simple and efficient procedure for the synthesis of 5'–aminoalkyl oligodeoxynucleotides," *Nuc. Acids Res.* 14(20):7985–7994 (1986).

Wilchek and Miron, "Limitations of N–hydroxysuccinimide esters in affinity chormatography and protein immobilization," *Biochem.* 26:2155–2161 (1987).

Wilchek et al., "Structure of a soluble super–active insulin is revealed by the nature of the complex between cyanogen–bromide–activated sepharose and amines," *P.N.A.S.* 72(3):1055–1058 (1975).

Yoshitake et al., "Conjugation of glucose oxidase from *Aspergillus niger* and rabbit antibodies using N–hydroxysuccinimide ester of n–(4–Carboxycyclohexylmethyl)–maleimide," *Eur. J. Biochem.* 101:395–399 (1979).

DNA—5'—OH

↓ T4 KINASE ATP

↓ (NH₂CH₂CH₂S-)₂

↓ 1. DTT
↓ 2.

DNA - 5' - OH

↓ T4 KINASE ATP

↓ $NH_2(CH_2)_6NH_2$

↓

↓ $NH_2CH_2CH_2NH_2$

↓ OLIGO- Br

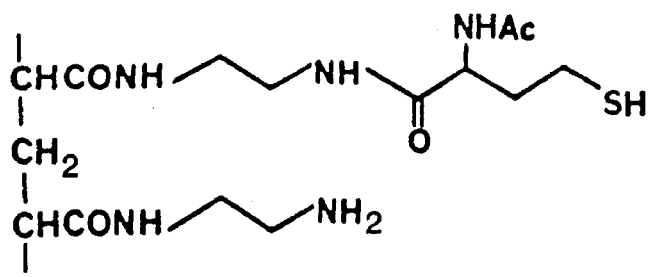
FIG. 6
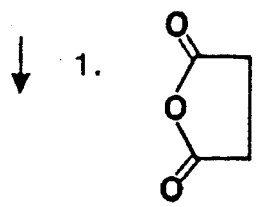
2. TRIS pH 8.5
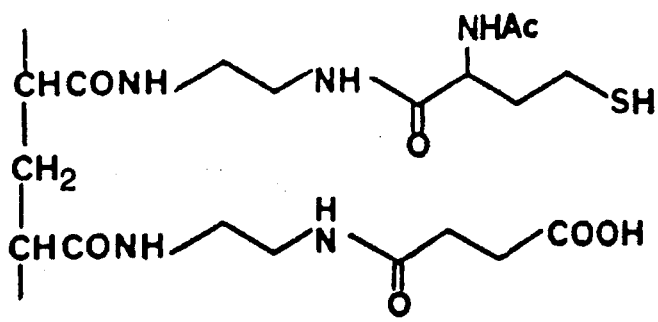
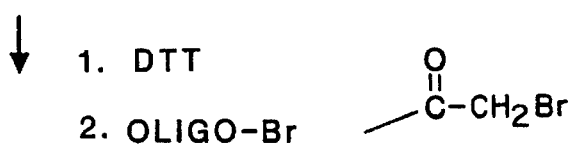
1. DTT
2. OLIGO-Br
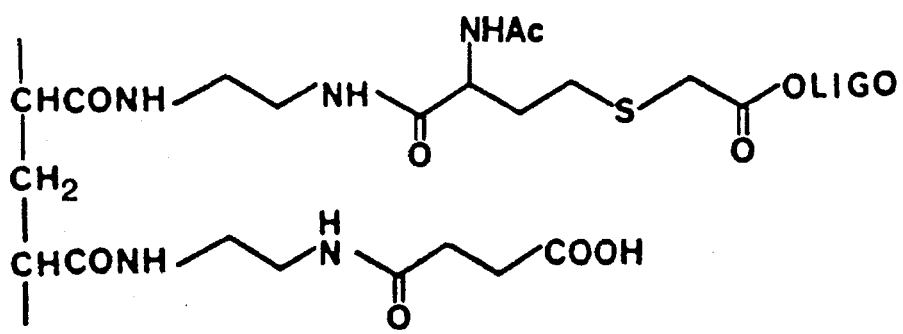

END-ATTACHMENT OF OLIGONUCLEOTIDES TO POLYACRYLAMIDE SOLID SUPPORTS FOR CAPTURE AND DETECTION OF NUCLEIC ACIDS

This application is a continuation-in-part of U.S. application Ser. No. 07/293,893, entitled "END-ATTACHMENT OF OLIGONUCLEOTIDES TO POLYACRYLAMIDE SOLID SUPPORTS FOR CAPTURE AND DETECTION OF NUCLEIC ACIDS,", filed Jan. 5, 1989, by Ghosh et al., U.S. Pat. No. 5,237,016. The subject matter of U.S. application Ser. No. 07/293,893 is hereby incorporated by reference in its entirety.

FIELD OF THE INVENTION

The present invention generally relates to the chemistry of the attachment of oligonucleotides to solid supports. More particularly, solid supports with oligonucleotides linked to the supports via their 5'-ends for capture and detection of nucleic acids, including single- and double-stranded DNA and RNA targets, are provided.

BACKGROUND OF THE INVENTION

It is often desirable to detect or quantify very small concentrations of nucleic acids in biological samples. Typically, to perform such measurements, the nucleic acid in the sample (i.e., the target nucleic acid) is hybridized to a detection oligonucleotide that contains at least ten contiguous nucleotides that are homologous to a portion of the target nucleic acid in the sample. In order to obtain a detectable signal proportional to the concentration of the target nucleic acid, either the target nucleic acid in the sample or the detection oligonucleotide is associated with a signal generating reporter element, such as a radioactive atom, a chromogenic or fluorogenic molecule, or an enzyme (such as alkaline phosphatase) that catalyzes a reaction that produces a detectable product. Numerous methods are available for detecting and quantifying the signal.

Following hybridization of a detection oligonucleotide with a target, the resulting signal-generating hybrid molecules must be separated from unreacted target and detection oligonucleotides. In order to do so, many of the commonly used methods immobilize the target nucleic acids or detection oligonucleotides on solid supports. This permits fractionation and identification of the hybridized nucleic acids. The target nucleic acid may be captured by oligonucleotides immobilized on solid supports. More frequently, so-called "sandwich" hybridization systems are used. These systems employ capture oligonucleotide covalently attached to a solid support for capturing detection oligonucleotide-target nucleic acid adducts formed in solution. Solid supports with linked oligonucleotides may also be used in methods of affinity purification.

Presently available solid supports to which oligonucleotides are linked include nitrocellulose or nylon membranes, activated agarose supports, or diazotized cellulose supports. Oligonucleotides containing an aldehyde or carboxylic acid group at the 5'-terminus have been covalently attached to non-porous polystyrene latex solid microspheres (Kremsky et al. (1987) *Nucl. Acids Res.* 15:2891). Although this method provides good end-attachment results, it is disadvantageous in that, at the end of the coupling reaction, non-covalently bound oligonucleotide must be removed by a tedious gel electrophoresis step. The presently available supports with attached oligonucleotides, however, have several other disadvantages in practice. Either the bonds between these supports and the oligonucleotides are not covalent, which allows release of the oligonucleotides from the support, or the supports have other shortcomings. For example, N-hydroxysuccinimide or cyanogen bromide activated polysaccharide affinity supports have a serious drawback in the leakage of ligands. This not only leads to misleading results but, even more importantly, poses health hazards when immunoaffinity-purified products produced by recombinant DNA synthesis are complexed with mouse monoclonal antibodies (see e.g., Wilchek et al. (1987) *Biochemistry* 26:2155 and Wilchek et al. (1975) *Proc. Natl. Acad. Sci. USA* 72:1055). Leakage of ligands from solid supports can also interfere with affinity purification. If the free ligand that leaks from the support is more effective as a binder than the insolubilized ligand, the free ligand will bind the target macromolecule essentially irreversibly, and prevent affinity adsorption to the support. Further, cyanogen bromide activation of polysaccharide supports leads to the formation of N-substituted isoureas on the surface of the matrix. These confer undesirable ion exchange properties on the support, which become problematic in affinity chromatography, when analytes, such as nucleic acids, are present in very minute concentrations.

Solid supports with linked oligonucleotides are also used in bead-based sandwich hybridization system (BBSHS) (see, e.g., EP 276,302 and Gingeras et al. (1989) *Proc. Natl. Acad. Sci. USA* 86:1173). According to this method, target nucleic acid and an oligonucleotide probe used for its detection, which is complementary to at least a region of the target, are hybridized. The obtained adduct is then captured by a second oligonucleotide that is complementary to a different region of the target and is end-attached to a solid support. The amount of the detection oligonucleotide associated with the solid support is directly related to the amount of the target captured. In this way, the BBSHS can be used to determine the amount of a single-stranded nucleic acid in a sample. Such assays typically use radioactively (e.g., $^{32}P$) labeled cloned DNA or synthetic oligonucleotides.

The potential sensitivity of assays that use support-bound oligonucleotides is a function of numerous parameters, including the level of non-specific background. In the presence of target, the non-specific background can result from various factors, including (1) hybridization of the detection and capture oligonucleotide to non-complementary sequences of the target nucleic acid; (2) hybridization of the detection oligonucleotide to the capture oligonucleotide; and (3) non-specific attachment of the detection oligonucleotide to the bead support or walls of the reaction vessel. The first two factors can be minimized by sufficiently stringent solution hybridization, capture, and wash conditions. The third factor (i.e., non-specific binding, including the percentage of oligonucleotides that are end-attached) appears to be an inherent property of the support and detections system used. In case of the conventionally used solid supports, particularly Sephacryl™ dextran beads, the percentage of oligonucleotides that are end-attached to the support is relatively low, about 50–55% (see, e.g., Ghosh et al. (1987) *Nucl. Acids Res.* 15:5353). A higher degree of end-attachment, however, is highly desirable because it would be result in greater capture potential of the immobilized oligonucleotide probe that would improve the sensitivity of assays in which such supports are used. Methods for improving the percentage of end-attachment and decreasing the level of non-specific attachment of the detection oligonucleotide to the bead support or walls of the reaction vessel are not presently available.

Therefore, it is an object herein to provide a method for preparing solid supports in which a substantial portion of the attached oligonucleotides are attached via their 5'-ends. It is also an object herein to provide solid supports in which a substantial portion of the attached oligonucleotides are attached via their 5'-ends.

SUMMARY OF THE INVENTION

Polyacrylamide supports with linked oligonucleotides such that a high percentage of the oligonucleotides are linked through their 5'-terminal phosphate group via a thioether linkage to the support are provided. Methods for preparing the polyacrylamide supports with oligonucleotides linked to the supports via a thioether linkage at their 5'-ends are also provided. The methods provide a means for covalent attachment of oligonucleotides to solid supports such that a high percentage, typically more than about 60%, preferably at least about 90%, and more preferably at least about 95%, of the attached oligonucleotides are attached to the supports via covalent thioether bonds at their 5'-ends. In practicing the methods, a thiol-derivatized oligonucleotide is reacted with a reactive carbon center-derivatized polyacrylamide support (e.g., bromoacetyl-derivatized polyacrylamide support), or conversely, a reactive carbon center-derivatized oligonucleotide (e.g., a bromoacetyl-oligonucleotide) is reacted with thiol-derivatized polyacrylamide support to produce a polyacrylamide support with 5'-end attached oligonucleotides. Thus, two general methods for preparation of the supports with linked oligonucleotides are provided. Both general methods provide a means for 5'-end attachment of greater than about 60%, preferably at least about 90%, and more preferably at least about 95%, of the oligonucleotides attached to the polyacrylamide solid supports. This results in immobilized oligonucleotides that exhibit superior direct capture ability for complementary oligonucleotides, double stranded DNA, and sandwich hybridization.

According to one general method, thiol-derivatized oligonucleotides are coupled with an active carbon center-derivatized polyacrylamide solid support (e.g., bromoacetyl-derivatized polyacrylamide solid support). Thiol-oligonucleotides can be prepared as described herein and by methods known to those of skill in the art (see, e.g., Li et al. (1987) Nucl. Acids Res. 15:5275; Chu et al. (1988) Nucl. Acids Res. 16:3671; see also references cited in Goodchild (1990) Bioconjugate Chemistry 1:165–186, 172).

According to the other general method, active carbon center-derivatized oligonucleotides (e.g., bromoacetyl oligonucleotides) are coupled with thiol-derivatized polyacrylamide solid support. Active carbon center-derivatized oligonucleotides and methods for preparation of such oligonucleotides are also provided.

The appropriately derivatized polyacrylamide supports may be prepared as described herein or by methods known to those of skill in the art. Polyacrylamide-based matrices, generally in the form of beads, are commercially available in a wide range of pore sizes, and are used routinely, for example, in affinity chromatography. Polyacrylamide supports with high exclusion limits are preferably employed. Preferably, the polyacrylamide support has an exclusion limit greater than about 2000 daltons, more preferably at least 400,000 daltons, and most preferably at least about $2 \times 10^7$ daltons.

Methods for chemical derivatization of these cross-linked polyacrylamide beads for use in affinity chromatography are known to those of skill in the art (see, e.g., Inman (1974) Meth. Enzymol. 34(B):30) and may be adapted as described herein for use in the methods. Hydrazide derivatives of cross-linked polyacrylamide, which serve as starting materials for the preparation of the other derivatives described herein, can be conveniently prepared by reacting the primary amide groups of the polyacrylamide support with hydrazine or, more generally, with alkyldiamines of the general formula $H_2N(CH_2)_aNH_2$ where a is 0 (for hydrazine) or 2 to about 20 (see, Inman (1974) Meth. Enzymol. 34(B):30; Inman et al. (1969) Biochem. 8(10):4074). For example, bromoacetyl-derivatized polyacrylamide matrices can be obtained by reacting the polyacrylamide-hydrazide derivatives with N-hydroxysuccinimide ester of bromoacetic acid, in a manner analogous to the reaction described by Bernatowicz et al. ((1986) Anal. Biochem. 155:95).

When using either coupling strategy, non-specific adsorption of the negatively charged nucleic acids to the polyacrylamide can be reduced by converting the residual functionalities of the solid supports (which do not participate in the coupling reaction) into other anionic groups, such as, but not limited to, carboxylic acid and trinitrophenyl groups. The resulting supports with mixed functionalities are particularly preferred. In preferred embodiments, the supports are first derivatized with hydrazine or alkyldiamines to produce an intermediate that may be used to produce either thiol-derivatized or active carbon center-derivatized supports. Thiol-derivatized supports also may be prepared by the coupling of the carboxyl groups with cystamine, followed by reduction with excess dithiothreitol (DTT).

Methods for capture of nucleic acids using the oligonucleotides attached to the polyacrylamide solid supports provided herein, either by direct capture or in sandwich hybridization formats are also provided.

In addition to methods provided above, all associated means for accomplishing such methods and preparing such products are contemplated. These means include (1) methods for preparation and purification of the detection and capture oligonucleotides, including synthesis or isolation from a natural source via restriction cleavage and subsequent purification; (2) preparation of oligonucleotide-signal elements or adducts (e.g., radioactive atom, enzyme, fluorescent, or chemiluminescent tags, mercury-based detectors, etc.) for use in hybridization with the target nucleic acids; and (3) hybridization techniques for hybridizing the target nucleic acid to the detection (and capture) oligonucleotide.

BRIEF DESCRIPTION OF THE DRAWINGS

FIG. 6 shows the acylation of thiol-derivatized Trisacryl™ polyacrylamide supports and the use of the products with mixed functionalities in coupling with bromoacetyl oligonucleotides.

DETAILED DESCRIPTION OF THE PREFERRED EMBODIMENTS

Figure 1:
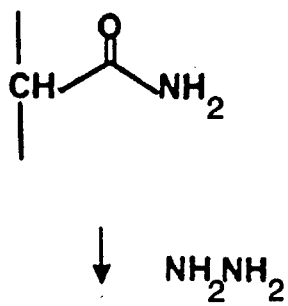
FIG. 1 illustrates the synthesis of bromoacetyl- (Reaction A) and sulfhydryl-containing (Reaction B) Bio-Gel™ polyacrylamide supports.
Figure 1:
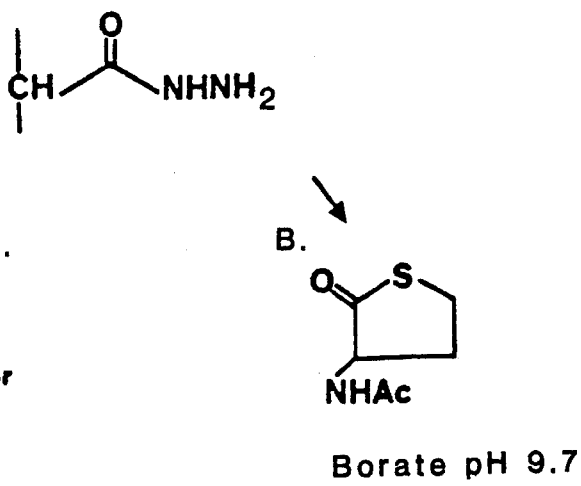
Figure 1:
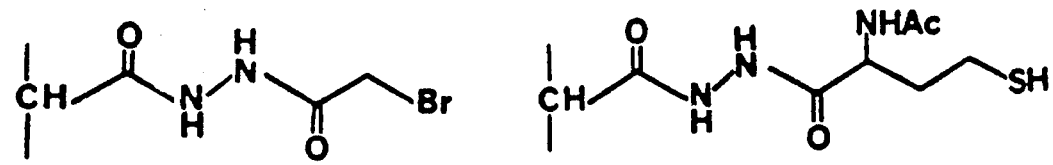

Unless defined otherwise, all technical and scientific terms used herein have the same meaning as is commonly understood by one of skill in the art to which this invention belongs. All publications mentioned herein are hereby incorporated by reference. All U.S. patents mentioned herein are hereby incorporated in their entirety by reference.

As used herein, in describing the process of linkage between oligonucleotides and polyacrylamide supports, the terms "attachment", "coupling", "tether", "binding", and "immobilization" are used interchangeably and refer to covalent linkage of oligonucleotides to the polyacrylamide supports.

As used herein, the term "detection oligonucleotide" or grammatical variations thereof refers to a nucleic acid (RNA or DNA) sequence (isolated from a natural source, synthetically produced, or a product of restriction digest) and carrying a reporter label that has sufficient complementarity with a target nucleic acid sequence such that under suitable conditions it is capable of hybridizing with said target sequence.

As used herein, the term "capture oligonucleotide" refers to a nucleic acid (RNA or DNA) fragment (isolated from a natural source, synthetically produced, or a product of restriction digest) that is attached to a polyacrylamide support, preferably substantially at its 5'-end, and that has sufficient complementarity with a target nucleic acid sequence (different from the sequence hybridized to the detection oligonucleotide) such that under selected conditions it forms stable hybrids with the target sequence. Typical detection and capture oligonucleotides are about 12 to 200 nucleotides, preferably about 15 to 40 nucleotides, in length and usually share at least about 12 bp, preferably about 25 bp, complementarity with the target nucleic acid sequence.

As used herein, "polyacrylamide supports" or "solid supports" are cross-linked polyacrylamide matrices that are commercially available in a wide range of pore sizes. Typical representatives of such matrices are "Bio-Gel™ polyacrylamide" beads, manufactured by Bio-Rad (USA) that are further categorized according to their exclusion volumes. The molecular weight exclusion limits of Bio-Gel™ polyacrylamide P-2, Bio-Gel™ P-10, Bio-Gel™ P-60 and Bio-Gel™ P-200 are 2000, 10000, 60000 and 200000 daltons, respectively. Bio-Gel™ polyacrylamide beads are exemplified herein, but any polyacrylamide supports, including those in which certain groups, such as the amide groups are substituted, may also be used. Other such polyacrylamide supports include, but are not limited to, Trisacryl™ polyacrylamide GF-200 (IBF Biotechnics, USA), which is produced by copolymerization of N-acryloyl-2-amino-2-hydroxymethyl-1,3-propane diol and has an exclusion limit of $2 \times 10^7$ daltons. In this resin the secondary amides contain 2-hydroxymethyl-1,3-propane diol substituents, each of its repeating units containing three hydroxymethyl groups and one secondary amide group. Consequently, this polymer is more hydrophilic in character than the Bio-Gel™ polyacrylamide resins.

As used herein, the term "reactive carbon center group" or "RCC group" refers to a group having a thiolphilic carbon atom which preferentially reacts with a thiol group as compared to other functional groups that are also present in the reaction mixture, including the amine and hydroxyl groups on either the polyacrylamide support, oligonucleotide or the solution in which the supports and oligonucleotides are dissolved or suspended.

As used herein, the term "leaving group" refers to a group, including, but not limited to, halogens (i.e., Br, Cl, I) or pseudo-halogens (e.g., —C≡N and —N≡N⁺), which, in the presence of a strong nucleophile, readily breaks away from a carbon atom to produce a reactive carbon center.

As used herein, the "thiol group" refers to a group containing a nucleophilic thiol moiety that is readily able to react, via a coupling type reaction, with a reactive carbon center to form a thioether bond.

As used in the formulas herein, the term "support" refers to polyacrylamide resin or polyacrylamide support, which contains repeating carboxamide groups. The repeating carboxamide groups are preferably of the general formula I:

wherein the heavy lines represent the polyacrylamide backbone and R is a hydrogen atom or an alkyl group containing 1 to 6 carbon atoms. R may, therefore, be hydrogen or a linear or branched hydrocarbon group. Preferably, R is hydrogen or —CH(CH$_2$OH)$_3$. Throughout this specification, unless indicated otherwise, heavy lines for chemical bonds (as shown in formula I) are intended to represent the polyacrylamide backbone.

As used herein, "oligonucleotide" refers to an oligomeric nucleic acid as opposed to a monomeric or polymeric nucleic acid. Oligonucleotides are nucleic acids including both single and double stranded RNA and DNA molecules that may be isolated from a natural source, may be synthesized or produced by restriction digest. One of skill in the art will recognize that longer oligonucleotides can be substituted for those which have been specifically exemplified herein, and the longer oligonucleotides will retain their ability to attach via thioether linkage such that more than 60%, preferably more than about 90%, and most preferably at least about 95%, are covalently attached via their 5'-ends. Typical oligonucleotides are 10–200 nucleotide bases long, but they may be substantially longer or they may be slightly shorter, depending upon the circumstances in which they are used. It is herein noted that the ability to link oligonucleotides via their 5'-ends to polyacrylamide support is not substantially influenced by sequence or length, but rather relies on the reactivity of the terminally linked thiol or reactive carbon center of the derivatized oligonucleotide for the derivatized support.

The term "TAS" is used to refer to the transcription amplification system disclosed in the co-pending U.S. application Ser. No. 07/202,978, which is a continuing application of U.S. application Ser. No. 07/064,141. This method involves using oligonucleotides to prime the synthesis of a double-stranded DNA copy (cDNA) of the target DNA or RNA sequence. In an embodiment of TAS, one of the oligonucleotides, primer A contains, within its sequence, the T7 RNA polymerase promoter binding sequence (PBS) attached to sequences complementary to the target sequence (TCS). Elongation from this primer by reverse transcriptase results in the generation of a single-stranded cDNA containing the T7 promoter at its 5'-end. A second primer oligonucleotide, primer B, is complementary to the first cDNA strand at some distance (100–300 bases) downstream of primer A. Primer B is used to initiate synthesis of the second cDNA strand, producing a double-stranded cDNA with the T7 RNA polymerase promoter attached. Incubation of the double-stranded cDNA with T7 RNA polymerase and ribonucleotide triphosphate will result in the synthesis of RNA transcripts from the cDNA. Additional amplification can be achieved by repeating TAS on the newly synthesized RNA.

As to other aspects of the methods and products provided herein, including preparation and purification of oligonucleotides, preparation of oligonucleotide-target nucleic acid adducts, methods for attachment of oligonucleotides to polyacrylamide supports, hybridization methodologies, detection and measurement of signals generated by properly hybridized nucleic acids, etc., reference is made to standard textbooks of molecular biology. See, for example, Maniatis et al. (1982) *Molecular Cloning: A Laboratory Manual*, Cold Spring Harbor Laboratory, New York, and the various references cited therein; Davis et al. (1986) *Basic Methods in Molecular Biology*, Elsevier Science Publishing, Inc., New York; and Hames et al. (1985) "*Nucleic Acid Hybridization*", IRL Press.

Polyacrylamide supports with oligonucleotides that are linked at their 5'-termini via a thioether covalent bond are provided. The thioether covalent bond is generated by virtue of the preferential reaction of a nucleophilic thiol group with a thiolphilic reactive carbon center group. These groups are hereinafter referred to collectively as the "reactive group(s)." Prior to coupling the oligonucleotides to the polyacrylamide supports, a nucleophilic thiol group is linked either to the polyacrylamide support or to the oligonucleotide and a reactive carbon center group is linked either to the polyacrylamide support or to the oligonucleotide.

1. Preparation of derivatized polyacrylamide supports

The polyacrylamide supports selected are those that, when derivatized with thiol groups or reactive carbon center groups and reacted with derivatized oligonucleotides, as described herein, more than about 60%, preferably at least 90%, and most preferably at least about 95%, of the oligonucleotides are bound to the support via thioether linkages at their 5'-ends. To prepare derivatized polyacrylamide supports, the primary amide groups of the polyacrylamide supports are at least partially converted into reactive carbon center groups or thiol groups prior to the attachment to the oligonucleotides. In preferred embodiments, the reactive carbon center derivatives and thiol derivatives are generated from hydrazide-derivatized supports.

Since the conversion of hydrazide supports into reactive carbon center-containing derivatives or thiol derivatives is not quantitative, the unconverted hydrazide functionalities are available for further derivatization; thus, if desired, they can be further converted into other groups, such as carboxyl, trinitrophenol, and similar groups. All of such derivatives are contemplated for used herein. It should be noted that, although the reactive carbon center- and thiol-derivatized polyacrylamide supports can be prepared from the respective hydrazide compounds, other synthetic routes, known to those of skill in the art, that are suitable for the production of polyacrylamide supports with the primary amide groups that are at least partially converted into reactive carbon center groups or thiol groups (see, e.g., Inman (1974) *Meth. Enzymol.* 34(B):30) may also be used.

Before further derivatization, the polyacrylamide matrices, such as Bio-Gel™ polyacrylamide beads, are treated with hydrazine or alkyldiamines, essentially following the procedure of Inman ((1974) *Meth. Enzymol.* 34(B):30) and/or Inman et al. ((1969) *Biochem.* 8(10) 4074). Depending on the hydrazine or diamine concentrations, reaction temperatures, and reaction times, hydrazide supports with various substitution levels of the hydrazide functionality may be obtained. The reaction can be carried out at room temperature or at higher temperatures (see, Inman (1974) *Meth. Enzymol.* 34(B):30). Hydrazide group densities may be measured by the methods known to those of skill in the art (see, e.g., Inman (1974) *Meth. Enzymol.* 34(B):30). Polyacrylamide resins with different exclusion limits can be employed, the higher exclusion limits being preferred. According to a particularly preferred embodiment, polyacrylamide supports having large pore sizes, in particular those with exclusion limits over 400,000 daltons, most preferably about $2 \times 10^7$ daltons, such as Trisacryl™ polyacrylamide GF 2000 (IBF Biotechnics, USA), are used.

Although the non-specific binding of [$^{32}$P]-labeled oligonucleotides was found to be low and not dependent on the level of substitution of the hydrazide functionalities on hydrazide-derivatized Bio-Gel™ polyacrylamide resins, hydrazide-derivatized supports did not perform well in binding experiments with enzyme-oligonucleotide conjugates (see, e.g., Table III below), primarily due to increased non-specific binding, principally attributed to the enzyme component of the conjugate. This problem was thought to be eliminated by further derivatization of the supports.

According to a particularly preferred embodiment, polyacrylamide supports with exclusion limits of about $2 \times 10^7$ daltons are employed. A typical support from this group is Trisacryl™ polyacrylamide GF-2000 (IBF Biotechnics, USA). Since, as hereinabove described, the amide hydrogens of this polyacrylamide resin are substituted with 2-hydroxymethyl-1,3-propane diol groups, before further derivatization, reactive amine groups need to be introduced, for example by transamidation with ethylene diamine. This reaction is carried out at slightly elevated temperatures, preferably at about 90° C. Thiol-derivatives of these supports are prepared in an analogous manner to the preparation of the thiol-derivatized Bio-Gel™ polyacrylamide products. To reduce electrostatic interactions between the positively charged amine groups and the negatively charged oligonucleotide backbone, the residual unreacted amine groups on the Trisacryl™ polyacrylamide supports are preferably acylated either with glutaric anhydride or succinic anhydride. The substitution level of the sulfhydryl groups on the Trisacryl™ polyacrylamide-SH supports, determined by titration of the sulfhydryl functionalities with DTNB, is in the range of about 10 to about 16 µmoles/g. With these supports, the coupling efficiencies to bromoacetylated oligonucleotides is about 20%, and the level of end-attachment is extremely high (about 97%). The oligonucleotide substitution level of these supports is about 60 pmoles oligonucleotide/gram support.

A. Attachment of Nucleophilic Thiol Groups to Polyacrylamide Supports

Thiol groups for use herein include groups having at least one nucleophilic thiol moiety attached to the polyacrylamide support, wherein the thiol moiety can react with a reactive carbon center attached to an oligonucleotide (as described in subsection 1.B below) to form thioether covalent bonds. Suitable thiol reactants contain a carbonyl or similar double bonded group for reaction with the primary amine group on the derivatized support. One preferred thiol reactant is of general formula II:

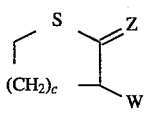

(II)

wherein Z is oxygen or $NH_2^+$; c is an integer equal to 1 or 2 and W is hydrogen or $-NHC(=O)R'$ where R' is an alkyl group containing 1 to 6 carbon atoms. Preferably, Z is oxygen or $NH_2^+$, c is 1, and W is hydrogen or $-NHC(=O)CH_3$. See, e.g., Lambert et al. (1983) *Biochem.* 22:3913; Lambert et al. (1981) *J. Mol. Biol.* 149:451. Another preferred thiol reactant is of general formula III:

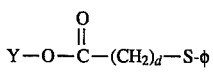

(III)

wherein d is an integer equal to 2 to 6; $\Phi$ is $-SR''$ or $-C(=O)R'''$ where R'' is 2-pyridyl, 3-carboxy-4-nitrophenyl, 5-nitro-2-pyridyl, or similar group and R''' is an alkyl group having 1 to 6 carbon atoms; and Y is an organic group suitable for forming an active ester which will readily react with the primary amine on the derivatized support. Examples of suitable Y groups include p-nitrophenyl, N-succinimidyl, N-sulfosuccinimidyl, and the like. Preferably, d is 2 to 6; $\Phi$ is $-SR''$ where R'' is 2-pyridyl or $-C(=O)CH_3$; and Y is N-succinimidyl or N-sulfosuccinimidyl. Specific examples of suitable thiol reactants of formula III include N-succinimidyl-3-(-2-pyridyldithio) propionate and N-succinimidyl S-acetyl thioacetate (see, e.g., Duncan et al. (1983) *Anal. Chem.* 132:68; Carlson et al. (1978) *Biochem. J.* 173:723; Gordon et al. (1987) *Proc. Nat. Acad. Sci. USA* 84:308; Gaur et al. (1989) *Nucl. Acids Res.* 17(11):4404).

The thiol groups are attached to the polyacrylamide support through the amide groups on the support. The amide groups of the polyacrylamide are first reacted with hydrazine or alkyldiamines as illustrated in the following reaction:

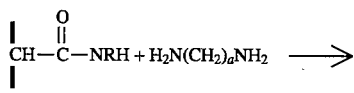

(Eq. 1)

wherein R is a hydrogen atom or an alkyl group containing 1 to 6 carbon atoms and a is an integer equal to 0 or 2 to 20. Preferably R is hydrogen and a is 0 or 2 to 6; more preferably R is hydrogen and a is 0, 2, or 6. The terminal amine groups of the reaction product of Equation 1 are then reacted with thiol-containing compounds II and III as illustrated in the following Equations 2 and 3:

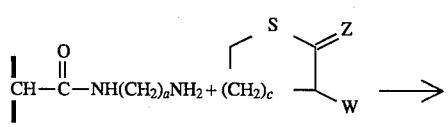

(Eq. 2)

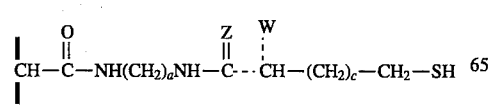

-continued and

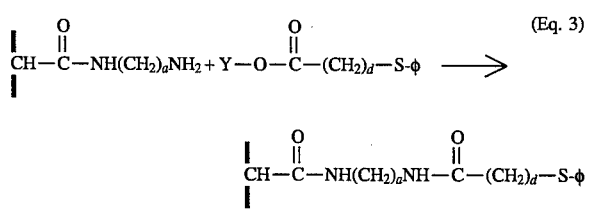

(Eq. 3)

wherein a is an integer equal to 0 or 2 to 20; c is 1 or 2; Z is oxygen or $NH_2^+$; W is hydrogen or $-NHC(=O)-R'$ where R' is an alkyl group having 1 to 6 carbon atoms; d is an integer from 2 to 6; $\Phi$ $-SR''$ or $-C(=O)R'''$ where R'' is 2-pyridyl, 3-carboxy-4-nitrophenyl, 5-nitro-2-pyridyl, or similar group and R''' is an alkyl group having 1 to 6 carbon atoms; and Y is an organic group which forms an active ester which readily reacts with the primary amine groups in the support as shown in Equation 3.

The thiol derivatized polyacrylamide supports formed in Equations 2 and 3 can be reacted with oligonucleotides containing a reactive carbon center. If $\Phi$ is $-SR''$ in Equation 3, whereby the thiol derivatized support contains a disulfide linkage, the disulfide should be reduced to a $-SH$ group with a conventional reducing agent (e.g., dithiothreitol) before reacting with a reactive carbon center attached to a oligonucleotide.

B. Attachment of Reactive Carbon Center Groups to Polyacrylamide Supports

Reactive carbon center groups for use herein include groups having at least one thiolphilic carbon atom which preferentially reacts with thiol groups from the thiol-derivatized oligonucleotides (as described in subsection 2.B below) to form thioether covalent bonds. In particular, thiolphilic reactive carbon centers include, but are not limited to, the α-carbon of a carbonyl compound in which the α-carbon is substituted with a good leaving group, the β-carbon in an α,β-unsaturated carbonyl compound (as in, for example, a ketone, ester, or amide), and other such groups known to those of skill in the art having a carbon atom which is highly reactive with a nucleophilic thiol group.

Suitable reactive carbon center reagents include α-halocarbonyls of general formula IV

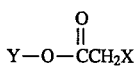

(IV)

wherein X is a good leaving group and Y is an organic group suitable for forming an active ester which will readily react with the primary amine on the derivatized oligonucleotides. Examples of good leaving groups include halogens (i.e., Br, Cl, and I) and pseudo-halogens (i.e., $-C\equiv N$ and $-N=N^+$). Examples of suitable Y groups include p-nitrophenyl, N-succinimidyl, N-sulfosuccinimidyl, and the like. One preferred reactive carbon center group is bromoacetyl which can be derived from bromoacetic acid-N-hydroxysuccinimide ester. Other suitable reactive carbon center reagents include α,β-unsaturated carbonyls of the general formula V

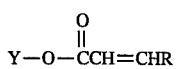

(V)

wherein R is hydrogen or an alkyl group containing 1 to 6 carbon atoms and Y is an organic group suitable for forming an active ester which will readily react with the primary amine on the derivatized oligonucleotides. Examples of suitable Y groups include p-nitrophenyl, N-succinimidyl, N-sulfosuccinimidyl, and the like. Other suitable reactive carbon center reagents include α,β-unsaturated carbonyls of the general formula VI

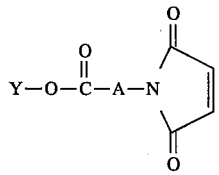
(VI)

wherein A is a linking group of general formula $-(CHR)_m-$, $-C_6H_4-$, $-C_6H_{10}-$, $-(CHR)_mC_6H_{10}-$, or $-C_6H_{10}(CHR)_m-$ where m is an integer equal to 1 to 20, R is hydrogen or an alkyl group containing 1 to 6 carbon atoms, and Y is an organic group suitable for forming an active ester which will readily react with the primary amine on the derivatized oligonucleotide. Examples of suitable Y groups include p-nitrophenyl, N-succinimidyl, N-sulfosuccinimidyl, and the like. One preferred reactive carbon center reactant of formula VI is succinimidyl 4-(N-maleimidomethyl) cyclohexane-1-carboxylate (i.e., where Y is N-succinimidyl and A is $-C_6H_{10}(CH_2)-$; see, Yoshitake et al. (1979) *Eur. J. Biochem.* 101:395; Mahan et al. (1987) *Anal. Biochem.* 162:163). Other preferred reactive carbon center reactants of formula VI include succinimidyl N-maleimidoalkyl-1-carboxylates (i.e., where Y is N-succinimidyl and A is $-(CH_2)_m-$ with m equal to 1, 2, or 5; see Keller (1975) *Helv. Chim. Acta* 58(2):531).

The polyacrylamide support is first treated with hydrazine or an alkyldiamine in essentially the same manner as shown in Equation 1 above to form

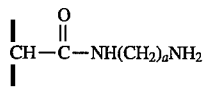
(VII)

wherein a is an integer equal to 0 or 2 to 20. Preferably, R is hydrogen and a is 0 or 2 to 6. The terminal amine groups of support VII can be reacted with the α-halocarbonyl compound IV as follows:

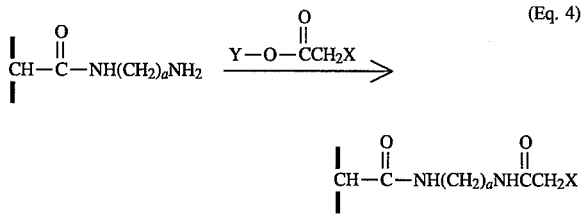
(Eq. 4)

wherein a is an integer equal to 0 or 2 to 20, preferably 0 or 2 to 6, and most preferably 0 or 2; X is a halogen (including Br, Cl, and I) or a pseudo-halogen (including $-C\equiv N$ and $-N=N^+$); and Y is an organic group suitable for forming an active ester which will readily react with the primary amine on the derivatized support. The terminal amine groups of support VII can be also reacted with the α,β-unsaturated carbonyl compound V as follows:

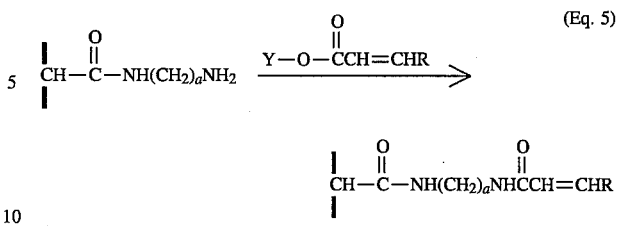
(Eq. 5)

wherein a is an integer equal to 0 or 2 to 20, preferably 0 or 2 to 6, and most preferably 0 or 2; R is hydrogen or an alkyl group containing 1 to 6 carbon atoms; and Y is an organic group suitable for forming an active ester which will readily react with the primary amine on the derivatized support. The terminal amine groups of support VII can be also reacted with the α,β-unsaturated carbonyl compound VI as follows:

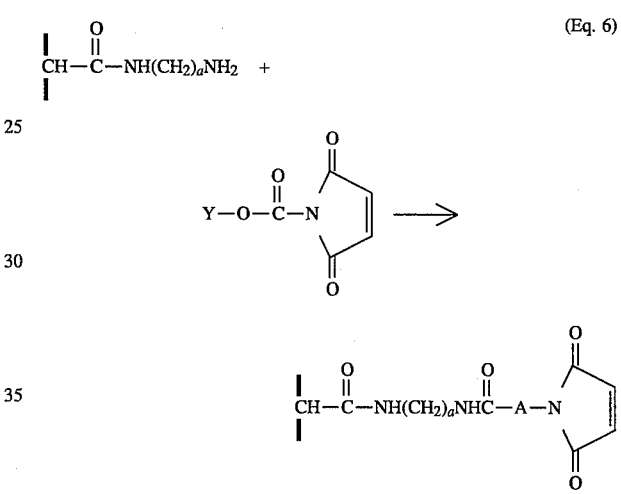
(Eq. 6)

wherein A is a linking group of general formula $-(CHR)_m-$, $-C_6H_4-$, $-C_6H_{10}-$, $-(CHR)_mC_6H_{10}-$, or $-C_6H_{10}(CHR)_m-$ where m is an integer equal to 1 to 20, R is hydrogen or an alkyl group containing 1 to 6 carbon atoms, and Y is an organic group suitable for forming an active ester which will readily react with the primary amine on the derivatized support. These reactive carbon center-derivatized polyacrylamide supports can be reacted with thiol-derivatized oligonucleotides (as described in subsection 2.B below) to form thioether covalent bonds.

2. Preparation of derivatized oligonucleotides

Oligonucleotides can be synthesized and purified by any method known in the art, for example using the solid-phase cyanoethyl phosphoramidite method and HPLC purification (Ghosh et al. (1987) *Nucl. Acids Res.* 15:5353). Alternatively, they can be isolated from natural sources or produced synthetically or by restriction enzyme cleavage and, if desired, tailored so as to be suitable for the intended use.

Thiol-derivatized oligonucleotides can be prepared, as hereinbefore described, by literature-known processes and as described herein. Bromoacetyl-derivatized oligonucleotides can be prepared as described herein. Further details of the preparation derivatized oligonucleotides are set forth in the Examples. Bromoacetylated oligonucleotides are prepared as described herein or may be prepared by methods that may be developed.

Thiol compounds, because of their greater nucleophilicity compared to amines, show enhanced reactivities towards compounds containing reactive carbon centers. Preferably, thiol-derivatized oligonucleotides are prepared using a [$^{32}$P]-labeled 5'-phosphorylated oligonucleotide in two steps: (1) reaction of the phosphate group with imidazole in the presence of a diimide and displacement of the imidazole leaving group with cystamine in one reaction step; and reduction of the disulfide bond of the cystamine linker with DTT. A similar procedure was described by Orgel et al. ((1986) *Nucl. Acids Res.* 14:651). The 5'-phosphorylated starting oligonucleotides are prepared as described by Maniatis et al. (1982) *Molecular Cloning: A Laboratory Manual*, Cold Spring Harbor Laboratory, New York, p. 122. Details of the synthesis of the thiol-derivatives are set forth in Example 1 c. The overall phosphate-to-thiol transformation obtained by this process was estimated to be 60–75% by polyacrylamide gel analysis of [$^{32}$P]-labeled products, and susceptibility of cleavage of 5'-$^{32}$PO$_4$ label of unreacted phosphorylated oligonucleotide by alkaline phosphatase treatment, as described in Example 1 d.

Oligonucleotides derivatized at their 5'-termini with, for example, bromoacetyl groups can be prepared by reacting 5'-aminohexylphosphoramidate oligonucleotides with bromoacetic acid-N-hydroxysuccinimide ester. The performance of the reaction is further illustrated in the examples. The phosphate-to-bromoacetamide transformation is about 60–70% determined by polyacrylamide gel analysis of the [$^{32}$P]-labeled products, and susceptibility of cleavage of 5'-$^{32}$PO$_4$ label of unreacted phosphorylated oligonucleotides to alkaline phosphatase treatment.

A. Attachment of Reactive Carbon Center Groups to Oligonucleotides

Essentially the same type of reactive carbon center groups can be attached to the oligonucleotides as can be attached to polyacrylamide support (i.e., reactive carbon center groups derived from compounds IV, V, and VI as discussed in subsection 1.B above). Reactive carbon center groups for use herein include groups having at least one thiolphilic carbon atom which preferentially reacts with thiol groups from the thiol-derivatized polyacrylamide support (as described in subsection 1.A above) to form thioether covalent bonds. In particular, thiolphilic reactive carbon centers include, but are not limited to, the α-carbon of the carbonyl compound IV in which the α-carbon is substituted with a good leaving group, the β-carbon in an α,β-unsaturated carbonyl compound (as in, for example, compounds V and VI), and other such groups known to those of skill in the art that present a carbon atom that is highly reactive with a nucleophilic thiol group. Such reactive carbon center groups are attached to the 5'-end of a oligonucleotide via a phosphate group. In one embodiment, a primary amine group is attached to the 5'-end of the oligonucleotide using hydrazine or an alkyldiamine reactant in the following reaction scheme:

   (Eq. 7)

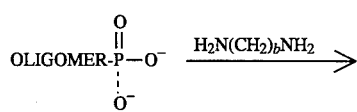

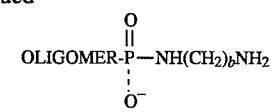

wherein b is an integer equal to 0 or 2 to 20, preferably 0 or 2 to 6, and most preferably is 0, 2, or 6. (See, e.g., Ghosh et al. (1989) *Anal. Chem.* 178:43; Wachter et al. (1986) *Nucl. Acids Res.* 14(20):7985; Tanaka et al. (1987) *Nucl. Acids Res.* 15(15):8209; Lund et al. (1988) *Nucl. Acids Res.* 16(22):10861; Chu et al. (1983) *Nucl. Acids Res.* 11(18):6513.) The primary amine derivatized oligonucleotide produced in Equation 7 can be reacted with reactive carbon center reagent IV to introduce the reactive carbon center as illustrated in the following equation:

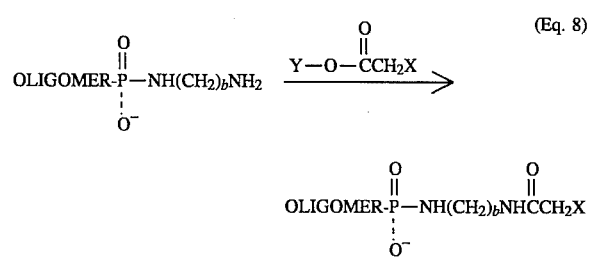

wherein b is an integer equal to 0 or 2 to 20, preferably 0 or 2 to 6, and most preferably 0, 2, or 6; X is a halogen (including Br, Cl, and I) or a pseudo-halogen (including —C≡N and —N=N$^+$); and Y is an organic group suitable for forming an active ester which will readily react with the primary amine on the derivatized oligonucleotide. The primary amine derivatized oligonucleotide produced in Equation 7 can also be reacted with reactive carbon center reagent V to introduce the reactive carbon center as illustrated in the following equation:

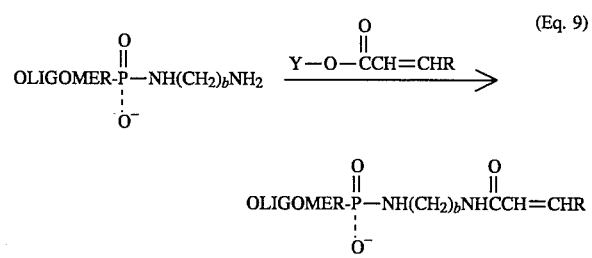

wherein b is an integer equal to 0 or 2 to 20, preferably 0 or 2 to 6, and most preferably 0, 2, or 6; R is hydrogen or an alkyl group containing 1 to 6 carbon atoms; and Y is an organic group suitable for forming an active ester which will readily react with the primary amine on the derivatized oligonucleotide. The primary amine derivatized oligonucleotide produced in Equation 7 can also be reacted with reactive carbon center reagent VI to introduce the reactive carbon center as illustrated in the following equation:

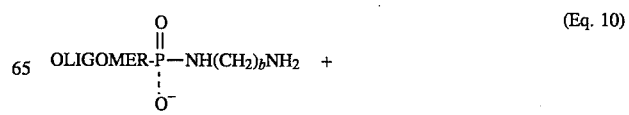   (Eq. 10)

-continued

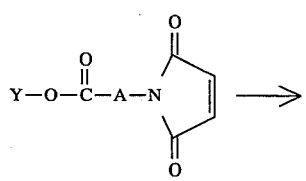

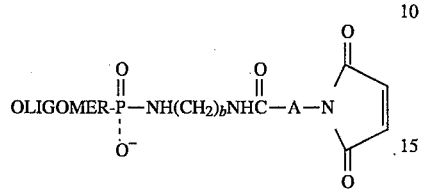

wherein b is an integer equal to 0 or 2 to 20, preferably 0 or 2 to 6, and most preferably 0, 2, or 6; A is a linking group of general formula $-(CHR)_m-$, $-C_6H_4-$, $-C_6H_{10}-$, $-(CHR)_m C_6H_{10}-$, or $-C_6H_{10}(CHR)_m-$ where m is an integer equal to 1 to 20, R is hydrogen or an alkyl group containing 1 to 6 carbon atoms, and Y is an organic group suitable for forming an active ester which will readily react with the primary amine on the derivatized oligonucleotide. Examples of suitable Y groups include p-nitrophenyl, N-succinimidyl, N-sulfosuccinimidyl, and the like. Preferably, b is 2 to 6; A is $-(CH_2)_m-$ or $-C_6H_{10}-$ where m is 1 to 5; and Y is N-succinimidyl or N-sulfosuccinimidyl.

In another embodiment, the primary amine group is attached to the oligonucleotide using Aminolink™ type reagents (Applied Biosystems, USA) or similar reagents as illustrated in the following reaction scheme:

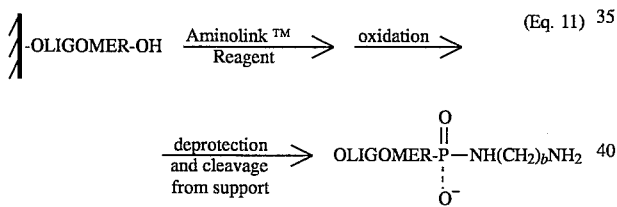
(Eq. 11)

wherein the solid vertical line with cross-hatching represents a suitable solid support; and b is an integer equal to 2 to 20 and, preferably, 2 to 6. Aminolink™ I and II, which are normally employed in automated DNA synthesizers, have the following structures:

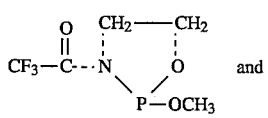
Aminolink™ I

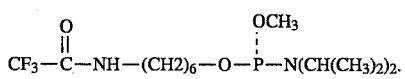
Aminolink™ II

For Aminolink™ I, b is 2 in Equation 11; for Aminolink™ II, b is 6 in Equation 11. (See, e.g., Bischoff et al. (1987) *Anal. Biochem.* 164:336.) The primary amine labeled oligonucleotides of Equation 11 can be treated with the same reactive carbon center reagents as the primary amine labeled oligonucleotides of Equation 7—i.e., the reagents used in Equations 8–10 can be employed to prepare corresponding oligonucleotides having reactive carbon centers.

B. Attachment of Nucleophilic Thiol Groups to Oligonucleotides

Essentially the same type of nucleophilic thiol groups can be attached to the oligonucleotides as can be attached to the polyacrylamide support (i.e., nucleophilic thiol groups as derived from thiol compounds II and III as discussed in subsection 1.A above). The oligonucleotide can be treated with hydrazine or an alkyldiamine in the essentially the same manner as shown in Equation 7 above to form

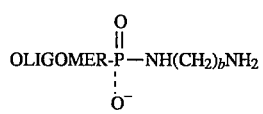
(VIII)

wherein b is an integer equal to 0 or 2 to 20. The terminal amine groups of oligonucleotide VIII can be reacted with the thiol compound II as follows:

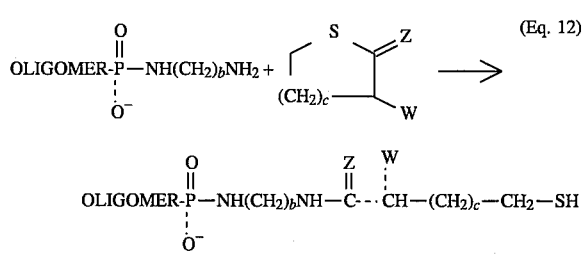
(Eq. 12)

wherein b is an integer equal to 0 or 2 to 20; c is 1 or 2; Z is oxygen or $NH_2^+$; and W is hydrogen or $-NHC(=O)-R'$ where R' is an alkyl group having 1 to 6 carbon atoms. Preferably, b is 0 or 2 to 6; c is 1; Z is oxygen; and W is hydrogen or $-NHC(=O)CH_3$. The terminal amine groups of oligonucleotide VIII can also be reacted with the thiol compound III as follows:

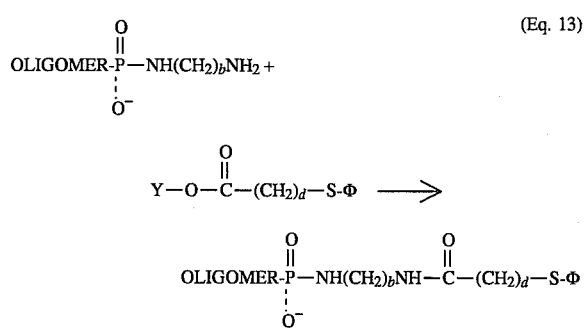
(Eq. 13)

wherein b is an integer equal to 0 or 2 to 20; d is an integer equal to 2 to 6; Φ is $-SR''$ or $-C(=O)R'''$ where R'' is 2-pyridyl, 3-carboxy-4-nitrophenyl, 5-nitro-2-pyridyl, or similar group and R''' is an alkyl group having 1 to 6 carbon atoms; and Y is an organic group which forms an active ester which readily reacts with the primary amine groups in the oligonucleotide in Equation 13. If a disulfide is formed (i.e., if Φ is $-SR''$), the disulfide should be reduced to a $-SH$ group with a conventional reducing agent (e.g., dithiothreitol) before reacting with a reactive carbon center attached to a polyacrylamide support.

Amine derivatized oligonucleotides prepared using Aminolink™-type reagents (as illustrated in Equation 11 above) can also be reacted with thiol compound II as follows:

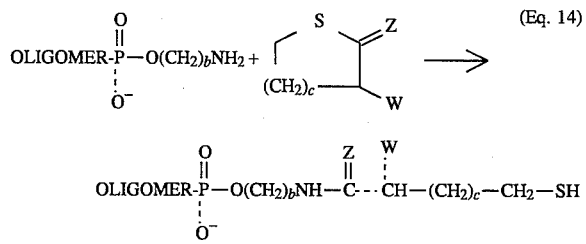
(Eq. 14)

wherein b is an integer equal to 2 to 20; c is 1 or 2; Z is oxygen or $NH_2^+$; and W is hydrogen or —NHC(=O)—R' where R' is an alkyl group having 1 to 6 carbon atoms. Preferably, b is 2 to 6; c is 1; Z is oxygen; and W is hydrogen or —NHC(=O)$CH_3$. Amine derivatized oligonucleotides prepared using Aminolink™-type reagents (as illustrated in Equation 11 above) can also be also reacted with thiol compound II as follows:

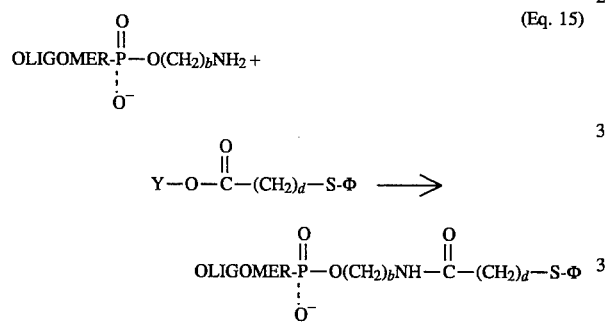
(Eq. 15)

wherein b is an integer equal to 2 to 20; d is an integer equal to 2 to 6; Φ is —SR" or —C(=O)R'" where R" is 2-pyridyl, 3-carboxy-4-nitrophenyl, 5-nitro-2-pyridyl, or similar group and R'" is an alkyl group having 1 to 6 carbon atoms; and Y is an organic group which forms an active ester which readily reacts with the primary amine groups in the oligonucleotide in Equation 15. If a disulfide is formed (i.e., if Φ is —SR"), the disulfide should be reduced to a —SH group with a conventional reducing agent (e.g., dithiothreitol) before reacting with a reactive carbon center attached to a polyacrylamide support.

Suitable thiol-derivatized oligonucleotides can be prepared by reacting a disulfide compound of general formula [$NH_2(CH_2)_eS$-]$_2$ (where each e is an integer independently equal to 2 to 20) with the 5'-end of a oligonucleotide having a phosphate group and then reducing the disulfide to a thiol using conventional reducing agents. The general synthesis is illustrated as follows:

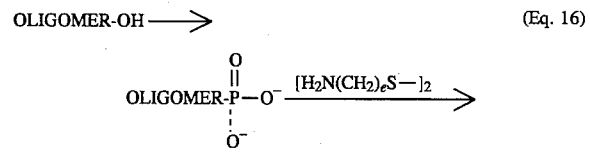
(Eq. 16)

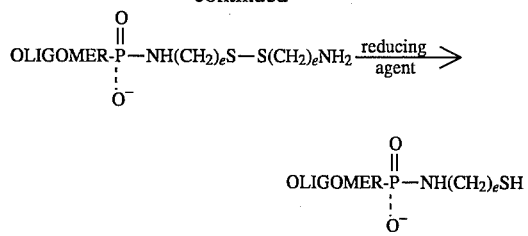

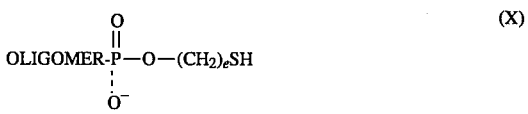

wherein each e is an integer independently equal to 2 to 20; preferably, e is 2 to 6 and, most preferably, e is 2.

Other suitable thiol-derivatized oligonucleotides having a thiol group attached to the 5'-end include compounds of the general formula:

$$\text{OLIGOMER-}\overset{O}{\underset{\overset{|}{O^-}}{\overset{\|}{P}}}\text{—O—}(CH_2)_e SH \quad\quad (X)$$

wherein e is an integer from 2 to 20, preferably from 2 to 6, and most preferably 2. Such oligonucleotides can be prepared using the general procedure of Connolly et al. (1985) *Nucl. Acids Res.* 13:4485.

The above thiol-derivatized oligonucleotides can be reacted with reactive carbon center-derivatized supports (as described in subsection 2.B above) to form thioether covalent bonds.

3. Coupling Reactions

The nucleophilic thiol groups attached to polyacrylamide support (as described in subsection 1.A above) are coupled with the reactive carbon center groups attached to oligonucleotides (as described in subsection 2.A). And the reactive carbon center groups attached to polyacrylamide support (as described in subsection 1.B above) are coupled with the nucleophilic thiol attached to oligonucleotides (as described in subsection 2.B above). The coupling reaction is carried out such that a large percentage (i.e., greater than 60%, preferably at least about 90%, and more preferably at least about 95%) of the linked oligonucleotides are linked to the support via a thioether linkage at their 5'-ends. To produce the supports with linked oligonucleotides, the derivatized oligonucleotides are coupled to the derivatized supports under suitable conditions. Generally, the coupling reaction is carried out in degassed buffer solutions under an inert atmosphere. Otherwise, it has been found that the precise conditions are not critical for the reaction. Exemplary polyacrylamide-oligonucleotide coupling products formed from coupling a thiol-derivatized support and a reactive carbon center-derivatized oligonucleotide include:

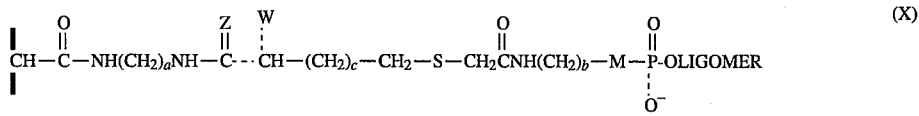

formed from coupling the thiol-derivatized support of Equation 2 and the reactive carbon center-derivatized oligonucleotide of Equation 8 (when M is —NH—) and wherein M is —NH— or oxygen; a is 0 or 2 to 20; b is 0 or 2 to 20 (when M is —NH-O or b is 2 to 20 (when M is —O—); c is 1 or 2; Z is oxygen or $NH_2^+$; and W is hydrogen or —NHC(=O)—R' where R' is an alkyl group having 1 to 6 carbon atoms;

formed from coupling the thiol-derivatized support of Equation 3 and the reactive carbon center-derivatized oligonucleotide of Equation 8 (when M is —NH—) and wherein M is —NH— or oxygen; a is 0 or 2 to 20; b is 0 or 2 to 20 (when M is —NH—) or b is 2 to 20 (when M is —O—); and d is 2 to 6;

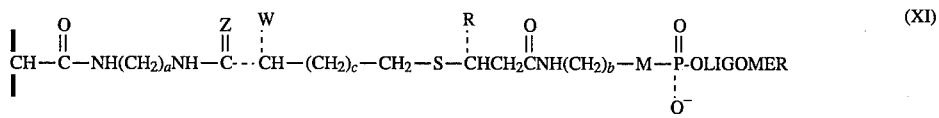

formed from coupling the thiol-derivatized support of Equation 2 and the reactive carbon center-derivatized oligonucleotide of Equation 9 (when M is —NH—) and wherein M is —NH— or oxygen; R is hydrogen or an alkyl group containing 1 to 6 carbon atoms; a is 0 or 2 to 20; b is 0 or 2 to 20 (when M is —NH—) or b is 2 to 20 (when M is —O—); c is 1 or 2; Z is oxygen or $NH_2^+$; and W is hydrogen or —NHC(=O)—R' where R' is an alkyl group having 1 to 6 carbon atoms;

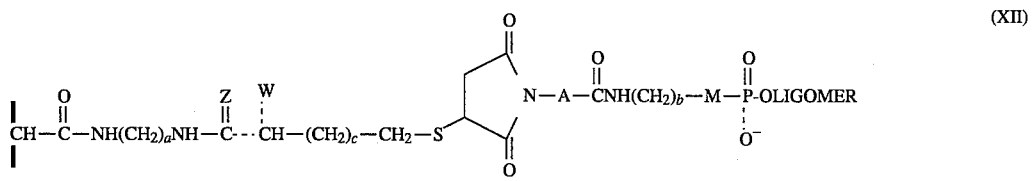

formed from coupling the thiol-derivatized support of Equation 2 and the reactive carbon center-derivatized oligonucleotide of Equation 10 (when M is —NH—) and wherein M is —NH— or oxygen; a is 0 or 2 to 20; b is 0 or 2 to 20 (when M is —NH—) or b is 2 to 20 (when M is —O—); c is 1 or 2; Z is oxygen or $NH_2^+$; W is hydrogen or —NHC(=O)—R' where R' is an alkyl group having 1 to 6 carbon atoms; and A is a linking group of general formula —$(CHR)_m$—, —$C_6H_4$—, —$C_6H_{10}$—, —$(CHR)_mC_6H_{10}$—, or —$C_6H_{10}(CHR)_m$— where m is an integer equal to 1 to 20 and R is hydrogen or an alkyl group containing 1 to 6 carbon atoms;

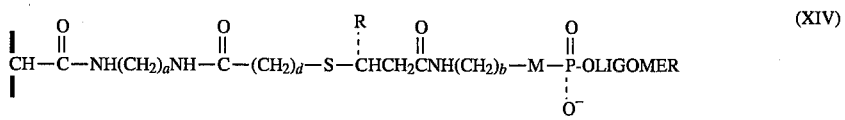

formed from coupling the thiol-derivatized support of Equation 3 and the reactive carbon center-derivatized oligonucleotide of Equation 9 (when M is —NH—) and wherein M is —NH— or oxygen; R is hydrogen or an alkyl group containing 1 to 6 carbon atoms; a is 0 or 2 to 20; b is 0 or (XIII)

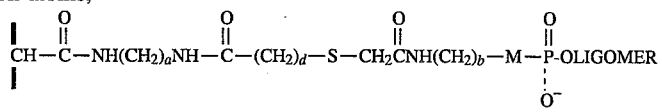

2 to 20 (when M is —NH—) or b is 2 to 20 (when M is —O—); and d is 2 to 6; and

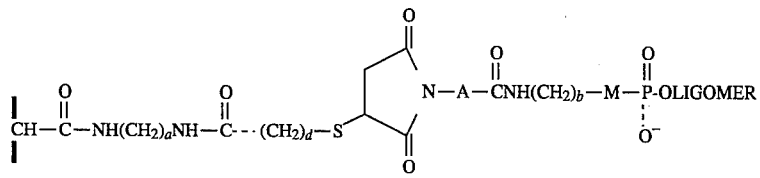 (XV)

formed from coupling the thiol-derivatized support of Equation 2 and the reactive carbon center-derivatized oligonucleotide of Equation 10 (when M is —NH—) and wherein M is —NH— or oxygen; a is 0 or 2 to 20; b is 0 or 2 to (when M is —NH—) or b is 2 to 20 (when M is —O—); d is 2 to 6; and A is a linking group of general formula —(CHR)$_m$—, —C$_6$H$_4$—, —C$_6$H$_{10}$—, —(CHR)$_m$C$_6$H$_{10}$—, or —C$_6$H$_{10}$(CHR)$_m$— where m is an integer equal to 1 to 20 and R is hydrogen or an alkyl group containing 1 to 6 carbon atoms.

Exemplary polyacrylamide-oligonucleotide coupling products formed from coupling a reactive carbon center-derivatized support and a thiol-derivatized oligonucleotide include:

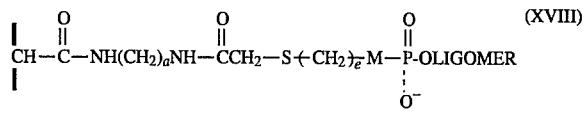 (XVIII)

formed from coupling the reactive carbon center-derivatized support of Equation 4 and the thiol-derivatized oligonucleotide of Equation 16 (when M is —NH—) or thiol-derivatized oligonucleotide IX (when M is oxygen) and wherein a is 0 or 2 to 20; and e is 2 to 20;

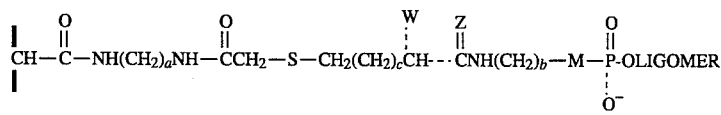 (XVI)

formed from coupling the reactive carbon center-derivatized support of Equation 4 and the thiol-derivatized oligonucleotide of Equation 12 (when M is —NH—) or Equation 14 (when M is —O—) and wherein M is —NH— or oxygen; a is 0 or 2 to 20; b is 0 or 2 to 20 (when M is —NH—) or b is 2 to 20 (when M is —O—); c is 1 or 2; Z is oxygen or NH$_2^+$; and W is hydrogen or —NHC(=O)—R' where R' is an alkyl group having 1 to 6 carbon atoms;

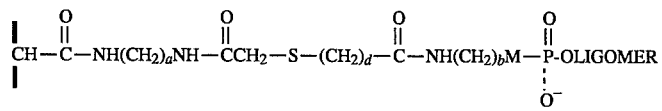 (XVII)

formed from coupling the reactive carbon center-derivatized support of Equation 4 and the thiol-derivatized oligonucleotide of Equation 13 (when M is —NH—) or Equation 15 (when M is —O—) and wherein M is —NH— or oxygen; a is 0 or 2 to 20; b is 0 or 2 to 20 (when M is —NH—) or b is 2 to 20 (when M is —O—); and d is 2 to 6;

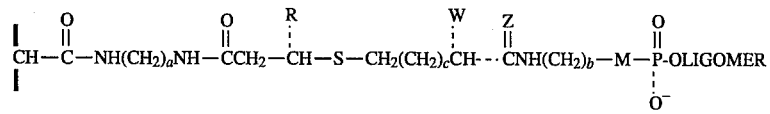 (XIX)

formed from coupling the reactive carbon center-derivatized support of Equation 5 and the thiol-derivatized oligonucleotide of Equation 12 (when M is —NH—) or Equation 14 (when M is —O—) and wherein M is —NH— or oxygen; R is hydrogen or an alkyl group containing 1 to 6 carbon atoms; a is 0 or 2 to 20; b is 0 or 2 to 20 (when M is —NH—) or b is 2 to 20 (when M is —O—); c is 1 or 2; Z is oxygen or $NH_2^+$; and W is hydrogen or —NHC(=O)—R' where R' is an alkyl group having 1 to 6 carbon atoms;

an alkyl group containing 1 to 6 carbon atoms; Z is oxygen or $NH_2^+$; and W is hydrogen or —NHC(=O)—R' where R' is an alkyl group having 1 to 6 carbon atoms;

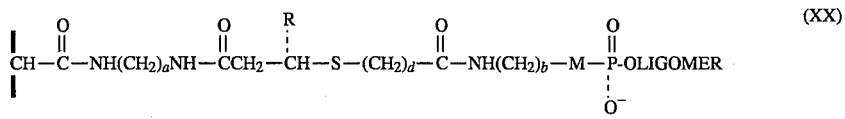
(XX)

formed from coupling the reactive carbon center-derivatized support of Equation 5 and the thiol-derivatized oligonucleotide of Equation 13 (when M is —NH—) or Equation 15 (when M is —O—) and wherein M is —NH— or oxygen; R is hydrogen or an alkyl group containing 1 to 6 carbon atoms; a is 0 or 2 to 20; b is 0 or 2 to 20 (when M is —NH—) or b is 2 to 20 (when M is —O—); and d is 2 to 6;

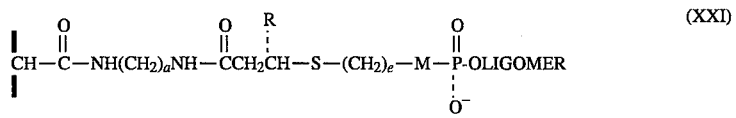
(XXI)

formed from coupling the reactive carbon center-derivatized support of Equation 5 and the thiol-derivatized oligonucleotide of Equation 16 (when M is —NH—) or the thiol-derivatized oligonucleotide IX (when M is oxygen) and wherein R is hydrogen or an alkyl group containing 1 to 6 carbon atoms; a is 0 or 2 to 20; and e is 2 to 20;

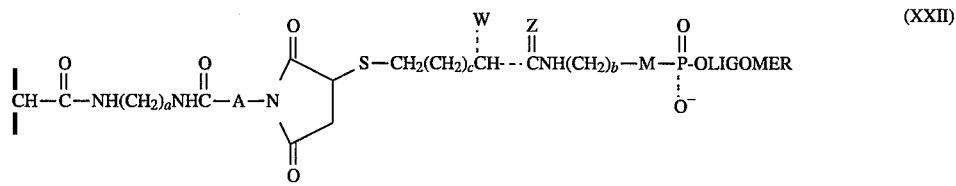
(XXII)

formed from coupling the reactive carbon center-derivatized support of Equation 6 and the thiol-derivatized oligonucleotide of Equation 12 (when M is —NH—) or Equation 14 (when M is —O—) and wherein M is —NH— or oxygen; a is 0 or 2 to 20; b is 0 or 2 to 20 (when M is —NH—) or b is 2 to 20 (when M is —O—); c is 1 or 2; A is a linking group of general formula —$(CHR)_m$—, —$C_6H_4$—, —$C_6H_{10}$—, —$(CHR)_mC_6H_{10}$—, or —$C_6H_{10}(CHR)_m$— where m is an integer equal to 1 to 20 and R is hydrogen or

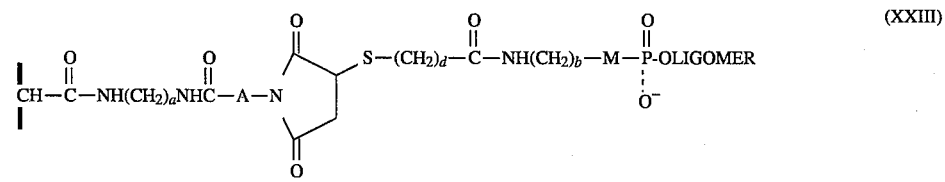
(XXIII)

formed from coupling the reactive carbon center-derivatized support of Equation 6 and the thiol-derivatized oligonucleotide of Equation 13 (when M is —NH—) or Equation 15 (when M is —O—) and wherein M is —NH— or oxygen; a is 0 or 2 to 20; b is 0 or 2 to 20 (when M is —NH—) or b is 2 to 20 (when M is —O—); d is 2 to 6; and A is a linking group of general formula —$(CHR)_m$—, —$C_6H_4$—, —$C_6H_{10}$—, —$(CHR)_mC_6H_{10}$—, or —$C_6H_{10}(CHR)_m$— where m is an integer equal to 1 to 20 and R is hydrogen or an alkyl group containing 1 to 6 carbon atoms; and

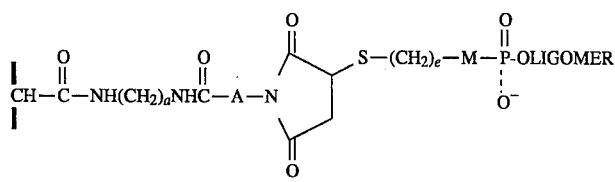

(XXIV)

formed from coupling the reactive carbon center-derivatized support of Equation 6 and the thiol-derivatized oligonucleotide of Equation 16 (when M is —NH—) or the thiol-derivatized oligonucleotide IX (when M is oxygen) and wherein a is 0 or 2 to 20; e is 2 to 20; and A is a linking group of general formula —$(CHR)_m$—, —$C_6H_4$—, —$C_6H_{10}$—, —$(CHR)_mC_6H_{10}$—, or —$C_6H_{10}(CHR)_m$— where m is an integer equal to 1 to 20 and R is hydrogen or an alkyl group containing 1 to 6 carbon atoms.

When the thiol group is attached to the polyacrylamide support, an excess of polyacrylamide support is used in the coupling reaction with the reactive carbon center-derivatized oligonucleotide in order to provide an overabundance of thiol groups that will out-compete the internal amines of the oligonucleotides for end-attachment to the reactive carbon centers, thereby resulting in a reproducible high percentage of 5'-end attachment of the oligonucleotide to the polyacrylamide support.

According to one embodiment, thiol-oligonucleotides are coupled to bromoacetyl-derivatized polyacrylamide supports. The bromoacetyl derivatives of polyacrylamide supports are preferably obtained by treatment of hydrazide functionalized supports with an excess of bromoacetic acid-N-hydroxysuccinimide ester, essentially following the procedure described by Bernatowicz et al. ((1986) *Anal. Biochem.* 155:95). The extent of derivatization can be determined by a two-step procedure. In the first step, the supports are exposed to a large excess of dithiothreitol (DTT) to effect a quantitative bromoacetyl-to-thiol functionality conversion. The thiol groups are then titrated with Ellman's reagent [5,5'-dithio-bis(2-nitrobenzoic acid)]. Under normal reaction conditions, the conversions usually range between 16–56%, therefore, the residual hydrazide groups are still available to further derivatization. Mixed carboxyl derivatives can be obtained by treating the bromoacetyl derivatized supports with excess glutaric anhydride, to effect a residual hydrazide-to-carboxyl transformation.

In non-specific binding experiments with oligonucleotide-alkaline phosphatase conjugates the bromoacetyl-derivatized supports perform considerably better than the hydrazide-derivatives. Non-specific binding is further reduced by the hydrazide-to-carboxyl transformation. It was found to be advantageous to silanize the Eppendorf tubes and have 1% BSA in the hybridization solutions to prevent adhesion of the oligonucleotide-enzyme conjugates to the walls of the tubes.

The covalent attachment of the bromoacetyl-oligonucleotides to thiol-derivatized polyacrylamide solid supports is illustrated in the examples. The coupling efficiencies are at least between about 3% and about 30%, depending on the pore size (molecular weight exclusion limit) of the solid support employed. More porous matrices with high exclusion limits provide substantially better coupling results than the highly cross-linked variants.

The thiol-derivatized oligonucleotides are, preferably, though not necessarily, coupled with the reactive carbon center-derivatized polyacrylamide supports under an inert atmosphere (e.g., a nitrogen atmosphere; see, also Example 1e). The attachment of thiol-oligonucleotides to the supports can be monitored using radiolabeled nucleic acids. The coupling efficiency of thiol-functionalized oligonucleotides to the bromoacetyl-derivatized solid supports is a function of the pH of the reaction, with pH of about 9.0 being preferred. There was considerable variability in the attachment efficiencies, but this is probably due to the susceptibility of the reactive thiol group to air oxidation in storage and during the course of the reaction. The overall attachment efficiencies were found to be between about 3.5% and 48%. Since the yields of the coupling experiments, however, are calculated as percentages of cpms of the total radioactivity introduced in the system, due to the incomplete conversion of the 5'-phosphorylated oligonucleotides to their thiol-derivatives, the actual yields are considerably higher. Moreover, following this method, more than 99% of the oligonucleotides are attached to the solid support through their 5'-termini. This is a striking advantage over other systems known in the art, for example Sephacryl™ dextran beads, where merely about 50–55% of the oligonucleotides are end-attached.

It is preferable to (1) use fresh thiol oligonucleotides for the coupling reaction, (2) degas all reaction solutions prior to use, and (3) carry out the coupling under an inert atmosphere (e.g., nitrogen or argon).

Using the reverse format, bromoacetyl-derivatized oligonucleotides are coupled with thiol-derivatized polyacrylamide solid supports. The introduction of thiol functionalities on polyacrylamide matrices can be achieved by reacting hydrazide-polyacrylamide supports with N-acetylhomocysteine thiolactone, essentially as described in Example 2a hereinafter. The extent of derivatization can be determined, by titration of the thiol group with Ellman's reagent, as hereinbefore described. The conversion usually is between about 4% and about 15%, and is strongly dependent on the amount of hydrazide groups in the solid supports; supports with higher hydrazide substitution levels being preferred. Since the conversion of hydrazide groups into thiol groups is low, there are always unreacted hydrazide groups left that are available for further derivatization. Matrices with mixed functionalities, in which the residual hydrazide groups are converted, for example, into carboxyl or trinitrophenyl groups, without modifying the thiol-functionalities, are easy to prepare by literature-known processes and may have advantages in certain hybridization reactions, by reducing non-specific absorption of the negatively charged nucleic acids, due to the anionic properties of carboxyl and trinitrophenyl groups. Treatment of the polyacrylamide supports with glutaric anhydride and/or iodoacetic acid converts the hydrazide and sulfhydryl functionalities to carboxylic groups. These supports were found to provide better non-specific adsorption results and are, therefore, preferred for use in direct capture experiments.

4. Hybridization properties of the polyacrylamide supports with end-attached oligonucleotides The hybridization potential of thiol-oligonucleotides immobilized on bromoacetyl polyacrylamide supports was evaluated using either a $^{32}$P-labeled oligonucleotide in a direct capture experiment, or a single-stranded 7Kb plasmid DNA target in a sandwich format. The oligonucleotides immobilized on polyacrylamide supports as described herein generally gave better results than oligonucleotides immobilized on Sephacryl™ dextran beads for direct capture of target oligonucleotides in this construction. The results were somewhat worse in case of sandwich capture of long target DNA.

The hybridization potential of bromoacetyl oligonucleotides immobilized on thiol-derivatized solid supports was tested by direct capture of oligonucleotide targets and in sandwich format, using TAS RNA transcripts. The results were similar to those obtained with the reverse format. While the oligonucleotides immobilized on thiol-polyacrylamide supports were clearly better in direct capture of oligonucleotides than Sephacryl™ dextran beads, their capture potential was less expressed in sandwich capture experiments, especially when long targets were to be identified.

In hybridization studies involving direct capture of radioactively labeled oligonucleotides, Trisacryl™ polyacrylamide-SH supports containing immobilized oligonucleotides, especially supports in which the unreacted sulfhydryl groups were alkylated with iodoacetate, performed particularly well. The oligonucleotides immobilized on Trisacryl™ polyacrylamide-SH supports showed excellent hybridization potential also in sandwich hybridization experiments, essentially carried out as hereinabove described. The signal-to-noise ratio was about 4-times higher in sandwich hybridization experiments performed with Trisacryl™ polyacrylamide supports than on Sephacryl™ dextran beads.

The bromoacetylated oligonucleotides coupled to thiol-derivatized polyacrylamide supports with reasonable yields, and the reproducability of the reaction is very good. In case of the reverse format, using thiol-oligonucleotides and bromoacetyl derivatized supports, the coupling efficiencies show greater variability, probably due to the higher susceptibility of thiol-oligonucleotides to oxidation. Both approaches, however, provide extremely good end-attachment results. Essentially all of the oligonucleotides (95% or more) are attached to the solid supports by their 5'-termini, by using either coupling methodology.

The hybridization potential of oligonucleotides immobilized on polyacrylamide solid supports as provided herein is very good in direct capture experiments, primarily due to the superior direct-capture ability of end-attached oligonucleotides. In sandwich hybridizations with TAS RNA products or long, single-stranded DNA fragments, the polyacrylamide supports having large pore sizes perform especially well in contrast to their highly cross-linked counterparts. The results can be further improved by functionalization of these porous supports, for example, with carboxyl groups. The best results were obtained with polyacrylamide supports having an exclusion limit of about $2\times10^7$ daltons (Trisacryl™ polyacrylamide GF 2000).

The direct capture and background properties of the oligonucleotides immobilized on the polyacrylamide solid supports produced by reacting bromoacetyl ester derivatized oligonucleotides with thiol-derivatized supports in which the detection oligonucleotides were labeled with alkaline phosphatase conjugates was examined. Although the background from non-specific binding was found to be low, use of the oligonucleotide-enzyme conjugates prevented the greater capture potential of polyacrylamide supports with end-attached oligonucleotides that are radiolabeled.

EXAMPLES

The following examples are included for illustrative purposes only and are not intended to limit the scope of the invention.

EXAMPLE 1

GENERAL MATERIALS AND METHODS a. Direct capture of $^{32}$P-labeled targets by oligonucleotide-derivatized supports The bead samples (50 mg) were aliquoted into 1 ml Eppendorf tubes, and the supernatant was removed after centrifugation. Prehybridization in 250 µl of 5x SSPE [0.75M NaCl, 50 mM NaH$_2$PO$_4$, pH 7.4, and 5 mM ethylene diamine tetracetate-4 Na (EDTA)], 10% dextran sulfate, 0.1% sodium dodecyl sulfate (SDS) was carried out at 37° C. for 30 minutes, after which the supernatant was drawn off. Samples of complementary and non-complementary $^{32}$P-labeled oligonucleotides (approximately 30 bases) were preincubated at 65° C. for 5 minutes and then added to the bead samples (typically 3.75 fmoles oligonucleotide/100 µl hybridization buffer). The beads were incubated at 37° C. for 1 hour with occasional shaking. After washing with 5 x 1 ml of 2x SSC (0.3M NaCl, 0.03M Na citrate, pH 7.0) at 37° C., the amount of label bound to the supports was determined by Cerenkov counting.

b. Sandwich hybridization of TAS-generated RNA transcripts on solid supports

Samples of Bio-Gel™ polyacrylamide (Bio-Rad, USA) or Trisacryl™ polyacrylamide (IBF Biotechnics, USA) (50 mg) were prehybridized as described above.

The target, DNA or RNA, was denatured at 65° C. for 5 minutes immediately prior to hybridization. Solution hybridization of the target RNA (0.5 fmoles) with a complementary, $^{32}$P-labeled detection oligonucleotide (5 fmoles) was performed in a total volume of 20 µl in 5x SSPE, 10% dextran sulfate, 0.1% SDS for 2 hours at 42° C. The sample was then diluted to 100 µl with hybridization buffer and added to the solid support. Sandwich hybridization was performed at 37° C. for 1 hour with occasional shaking. Finally, the beads were washed with 5 x 1 ml 2x SSC at 37° C. Non-complementary RNA target was used as a control to determine the level of non-specific binding in the assay.

c. Direct capture of alkaline phosphatase-oligonucleotide conjugates on solid supports Oligonucleotide-containing Bio-Gel™ polyacrylamide or Trisacryl™ polyacrylamide supports (50 mg) were prehybridized with 250 µl of 5x SSC, 10% dextran sulfate, 0.1% SDS, 1% bovine serum albumin fraction V (BSA) in 1 ml Eppendorf tubes for 30 minutes at 37° C. Complementary and non-complementary oligonucleotide-alkaline phosphatase conjugates were diluted with 0.1M Tris, 0.1M NaCl, 1% BSA, pH 7.5, and preincubated at 55° C. for 5 minutes. After addition of the conjugate (37.5 fmoles) in 100 µl of hybridization buffer, the mixture of conjugate and Sephacryl™ dextran beads was incubated at 42° C. for 1 hour with occasional shaking. The supports were washed with 4 x 1 ml of 2x SSC at 37° C. The bead samples and washes were treated with 1 ml 0.1 mM p-nitrophenyl phosphate in 0.1M Tris, 0.1M NaCl, 0.01M $MgCl_2$, pH 9.5. After development of color at room temperature for 1 hour, the formation of p-nitrophenolate was measured by reading the absorbance at 410 nm.

d. TNBS test for hydrazides and amines

Filtrates for hydrazide or amine-derivatized supports were tested for free hydrazide or ethylene-diamine as follows. Two ml of filtrate were treated with 1 ml of saturated $Na_2B_4O_7$ and 3 drops of 3% aqueous trinitrobenzene sulfonate (TNBS), with thorough mixing. The appearance of a purple or orange color after one minute indicated the presence of hydrazine or amine, respectively.

e. DTNB test for sulfhydryl and bromoacetyl substitution determination

A sample of derivatized support (1–20 mg wet weight) was reduced with 500 μl of 20 mM dithiothreitol (DTT) in 0.05M $K_2HPO_4$, 1 mM EDTA, pH 8.0, for 30 minutes in a 1-ml Eppendorf tube and washed with 3 x 1 ml of 0.05M $K_2HPO_4$, pH 8.0, after the supernatant had been removed. The beads were then treated with 1 ml of 1 mM 5,5'-dithiobis(2-nitrobenzoic acid) (DTNB) in 0.05M $K_2HPO_4$, pH 8.0. The absorbance of the supernatant was monitored at 412 nm after 15 minutes ($\epsilon$=13,600 for released thiophenolate).

EXAMPLE 2

PREPARATION OF HYDRAZIDE DERIVATIVES OF BIO-GEL™ POLYACRYLAMIDE BEADS

Hydrazide derivatives of Bio-Gel™ polyacrylamide beads (Bio-Rad, USA) were prepared using the procedure of Inman ((1974) *Meth. Enzymol.* 34(B):30). Typically, a 20 ml solution of 6M hydrazine at 50° C. was added to 1 gram of dry resin. After 40 minutes, the excess reagent was removed by washing the beads with 0.2M NaCl until the filtrate gave a negative test with 2,4,6-trinitrobenzene sulfonic acid (TNBS). The derivatized beads were dried under negative pressure for 15 minutes, weighed, and suspended in 10 mM Tris, 1 mM EDTA (TE), pH 8.0, or 0.1M $K_2HPO_4$, pH 8.0.

The non-specific binding of [$^{32}$P]-labeled oligonucleotides, alkaline phosphatase-oligonucleotide conjugates, alkaline phosphatase with BSA, and linker-derivatized alkaline phosphatase with BSA was determined with the above supports, and the results presented in Table I.

TABLE I

NON-SPECIFIC BINDING ON BIO-GEL™
POLYACRYLAMIDE P-60 HYDRAZIDE BEADS

| Bio-Gel™ polyacryl-amide Hydrazide | % Bound to Beads | | | | |
|---|---|---|---|---|---|
| | [$^{32}$P] O-ligo | Conju-gate | Alkaline Conjugate +BSA | Alkaline Phosphatase with BSA | Phos-phatase Linker W/BSA |
| 31 micro-mole/gm | 0.26 | 11.3 | 5.2 | 1.95 | 5.90 |
| 62 micro-mole/gm | 0.23 | 9.8 | — | — | — |
| 125 micro-mole/gm | 0.32 | 13.7 | 4.1 | — | — |
| 500 micro-mole/gm | 0.41 | 13.5 | 8.6 | 1.2 | 4.49 |

The non-specific binding of [$^{32}$P]-labeled oligonucleotides was low and was not dependent on the level of substitution of the hydrazide residues on Bio-Gel™ polyacrylamide. Backgrounds from enzyme-oligonucleotide conjugates were much higher (9.8–13.7%) when no BSA was used in the hybridization solutions. This indicated that the enzyme component of the conjugate was largely responsible for this interaction. The addition of BSA to the hybridization mixture was found to be partially effective in eliminating non-specific binding of the enzyme-oligonucleotide conjugate. Parallel experiments using alkaline phosphatase and alkaline phosphatase-linker show that derivatization of the enzyme with the linker was primarily responsible for the non-specific binding.

EXAMPLE 3

COVALENT ATTACHMENT OF THIOL-OLIGONUCLEOTIDES TO BROMOACETYL BIO-GEL™ POLYACRYLAMIDE BEADS a. Acylation of Bio-Gel™ polyacrylamide hydrazide beads with N-succinimidyl bromoacetate 1. Synthesis of N-succinimidyl bromoacetate. Bromoacetic acid (20 mmoles) was treated with dicyclohexylcarbodiimide (22 mmoles, 1.1 equivalents) and N-hydroxysuccinimide (22 mmoles) in 30 ml $CH_2Cl_2$ at 4° C. according to the procedure of Bernatowicz et al. ((1986) *Anal. Biochem.* 155:95) to give the N-succinimidyl bromoacetate as a white solid.

2. Acylation. A 1 gram (wet weight) sample of Bio-Gel™ polyacrylamide hydrazide beads (50 μmoles/dry gram) was washed with 2x 50 ml 0.1M $K_2HPO_4$, pH 7.0, and resuspended in 5 ml of this buffer. The suspension was cooled to 0° C. in an ice bath, and N-succinimidyl bromoacetate (10 mole equivalents relative to hydrazide groups) in 250 μl N,N-dimethylformamide (DMF) was added dropwise with stirring. The reaction mixture was allowed to come to room temperature over 30 minutes. After cooling to 0° C. again, another aliquot of N-succinimidyl bromoacetate was added and the reaction mixture was stirred for 30 minutes at room temperature. The beads were filtered through a sintered glass funnel (porosity C) and washed with 50 ml 0.1M $K_2HPO_4$, pH 7.0. The acylated beads were stored in 0.1M $K_2HPO_4$ at 4° C.

To determine the level of substitution, the supports were exposed to a large excess of DTT to effect a quantitative bromoacetyl-to-thiol functionality conversion. The thiol groups were then titrated with Ellman's reagent [5,5-dithiobis-(2-nitrobenzoic acid)] (see Example 1e). From Table II it can be seen that the conversion of hydrazide groups to bromoacetyl functionalities proceeded with an efficiency of 56%, 43%, and 40% for P-10, P-60, and P-200, respectively, while the reaction with the P-2 support was less efficient.

TABLE II

REACTION OF HYDRAZIDE WITH BROMOACETIC
ACID NHS ESTER POLYACRYLAMIDE
SUPPORTS

| Support Type | μmoles $NHNH_2$/g | Molar excess NHSBrAc | μmoles $CH_2Br$/g | % $NHNH_2$ converted |
|---|---|---|---|---|
| P-2-$CH_2Br$ (MW exclusion limit 2,000) | 50 | 20 | 8.0 | 16.0 |
| P-10-$CH_2Br$ (MW exclusion limit 10,000) | 50 | 20 | 27.9 | 55.8 |

TABLE II-continued

REACTION OF HYDRAZIDE WITH BROMOACETIC ACID NHS ESTER POLYACRYLAMIDE SUPPORTS

| Support Type | µmoles NHNH$_2$/g | Molar excess NHSBrAc | µmoles CH$_2$Br/g | % NHNH$_2$ converted |
|---|---|---|---|---|
| P-60-CH$_2$Br (MW exclusion limit 60,000) | 50 | 20 | 21.6 | 43.2 |
| P-200-CH$_2$Br (MW exclusion limit 200,000) | 50 | 20 | 20.3 | 40.5 |

TABLE III

NON-SPECIFIC BINDING WITH 50 FMOLES CONJUGATE (% BOUND)

| Type of Support | —NHNH$_2$ | —CH$_2$Br —NHNH$_2$ | —CH$_2$Br —COOH |
|---|---|---|---|
| P-2 | 1.57 | 1.01 | 0.71 |
| P-60 | 7.3 | 3.5 | 1.4 |

Non-specific binding experiments with oligonucleotide-alkaline phosphatase conjugates (see Example 1c) were carried out with three types of P-2 and P-60 supports (Table III).

A decrease in non-specific adsorption was observed for both supports when the hydrazide functionality was capped with bromoacetyl groups. Since the reaction of hydrazide supports with bromoacetic acid N-hydroxysuccinimide ester does not result in a quantitative conversion (see Table II, last column), the residual hydrazide groups are still available for derivatization.

b. Glutarylation of bromoacetyl Bio-Gel™ polyacrylamide beads

A 1.0 gram (wet weight) sample of bromoacetyl Bio-Gel™ polyacrylamide beads (50 µM hydrazide/dry gram) was washed with 0.1M NaCl and suspended in 20 ml of this solution in a glass beaker. To the stirred suspension was added 100 mg of glutaric anhydride. The pH of the suspension was maintained at 4.0–4.2 with 3M NaOH, while the reaction mixture was stirred for 15 minutes. Then, another 100 mg of anhydride was added, and the reaction mixture was stirred for a further 15 minutes. The beads were then washed with 3x 40 ml 0.1M K$_2$HPO$_4$, pH 7.0, by allowing the beads to settle in a conical tube and decanting the supernatant.

Figure 2:
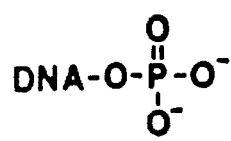
FIG. 2 shows the synthetic route of thiol-oligonucleotides and their coupling to bromoacetyl-derivatized Bio-Gel™ polyacrylamide supports. (The residual hydrazide groups are converted to carboxyl groups to lower non-specific binding.)
Figure 2:
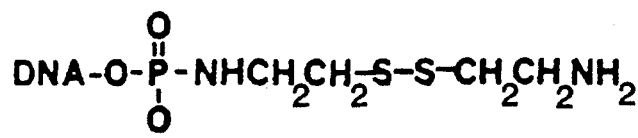
Figure 2:
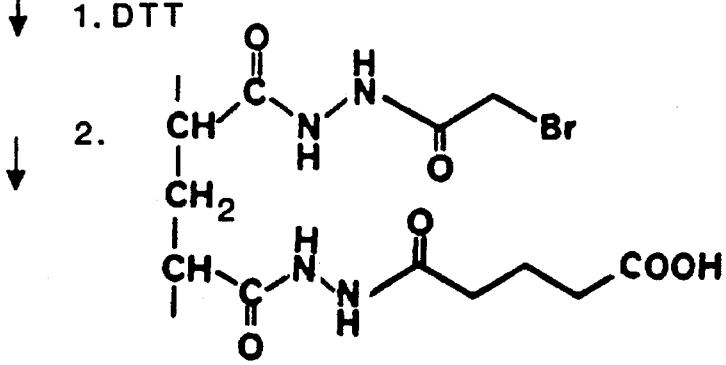
Figure 2:
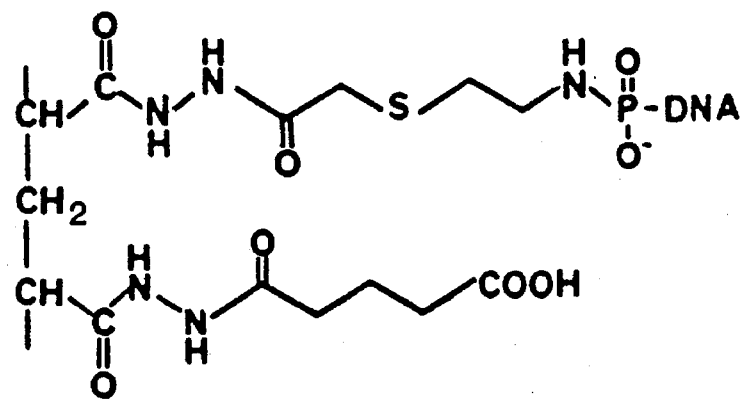

When the bromoacetyl supports were treated with excess glutaric anhydride, as described above, a hydrazide-to-carboxyl transformation was obtained. The carboxyl group in these bifunctional supports provided an additional reduction in non-specific binding of the enzyme-oligonucleotide conjugates (Table III, column 3).

c. One-step preparation of 5'-cystaminyl phosphoramidate derivatives of oligonucleotides The 5'-phosphorylated oligonucleotide (Maniatis et al. (1982) *Molecular Cloning: A Laboratory Manual*, Cold Spring Harbor Laboratory, New York) in a silanized Eppendorf tube was treated with 300 µl of a 0.1M imidazole, 0.15M 1-ethyl-3-(3-dimethylaminopropyl)-carbodiimide·HCl (EDC), 0.25M cystamine dihydrochloride, pH 6.0, and let stand at room temperature overnight. The modified oligonucleotides were precipitated with ethanol/LiCl, washed with 300 µl H$_2$O, and precipitated again. Yields of 86% were obtained using this procedure. The reaction is illustrated in FIG. 2.

d. Determination of level of cystamine attachment to 5'-phosphorylated oligonucleotides A 50-pmole sample of $^{32}$P-labeled cystaminyl-derivatized oligonucleotide was treated with 1 µl stock calf intestine alkaline phosphatase (Boehringer Mannheim, EIA grade) and the volume made up to 100 µl with 0.1M Tris, 0.1M NaCl, 0.01M MgCl$_2$, pH 9.5. The reaction was allowed to proceed for 2 hours. The sample was then applied on a 5 ml column of Sephadex G-50 and eluted with TE, pH 8.0. The first and second radioactive peaks were collected, corresponding to cystaminyl-derivatized oligonucleotides and free inorganic phosphate (cleaved from 5'-phosphorylated oligonucleotide), respectively. The peaks were counted by Cerenkov counting to estimate the yield of cystamine attachment.

e. Covalent attachment of 5'-cystaminyl-derivatized oligonucleotides to bromoacetyl-Bio-Gel™ polyacrylamide beads The cystaminyl-containing oligonucleotide was reduced with 300 µl 0.1M DTT, 0.2M HEPES, 0.001M EDTA, pH 7.7, for 1 hour at room temperature. The product was precipitated with EtOH/LiCl and washed twice with 0.2M HEPES, 0.001M EDTA. Typically, 50 mg of beads were treated with 25 pmoles of reduced oligonucleotide in 150 µl 0.1M K$_2$HPO$_4$, pH 9.0, and agitated under N$_2$ on a rotary mixer overnight. As a control to determine non-specific binding, a 5'-phosphorylated oligonucleotide was added to a sample of beads under the same conditions. The beads were washed with: (a) 3x 1 ml 0.1M Na$_2$P$_2$O$_7$, pH 7.5, and (b) 3x 1 ml 0.015M NaOH, pH 12. $^{32}$P-labeled oligonucleotides were used as controls to estimate end-attachment efficiencies. Oligonucleotides 86-31 and 87-416, which were used in the experiments have the following nucleotide sequences:

Sequence ID No. 1: 5' GCACACAAGTAGACCCTGAAC-TAGCAGACCA 3' (86-31)

Sequence ID No. 2: 5' AACCAATAAGAAGATGAGGCAT-AGCAGCA 3' (87-416).

The attachment of the thiol-derivatized oligonucleotides to the bromoacetyl-Bio-Gel™ polyacrylamide supports was monitored using radiolabeled nucleic acids, and the results are summarized in Table IV.

Since the yields of the coupling experiments are percentages of cpms of the total radioactivity introduced in the reaction, the actual yields are in fact higher, due to the incomplete conversion of 5'-phosphorylated oligonucleotides to their thiolated derivatives. Substantially all of the oligonucleotides were end-attached via thioether bonds following this coupling strategy. The variability in the attachment efficiencies (see entries 3–6, Table IV), was ascribed to the susceptibility of the reactive thiol group to air oxidation in storage or during the course of the reaction. While the overall attachment efficiencies of oligonucleotide to polyacrylamide supports (3–48%) were lower than to Sephacryl™ dextran (70%), this coupling strategy provides a superior method for obtaining end-attached oligonucleotides.

TABLE IV

COUPLING YIELDS[1] OF BROMOACETYL SUPPORTS WITH THIOL-OLIGONUCLEOTIDES

| Type of Support | % 86-31-SH bound | % 86-31-PO4 bound | % end-attachment | %[2] 87-416-SH bound | % 87-416-PO$_4$ bound | % end-attachment |
|---|---|---|---|---|---|---|
| 1 P-2-CH$_2$Br | 3.46 | 0.08 | 98 | | | |
| 2 P-10-CH$_2$Br | 9.51 | 0.44 | 95 | | | |
| 3 P-60-CH$_2$Br | 15.82 | 0.28 | 98 | | | |
| 4 P-60-CH$_2$Br | 36.7 | 0.84 | 98 | | | |
| 5 P-60-CH$_2$Br | 48.4 | 0.15 | 100 | | | |
| 6 P-200-CH$_2$Br | 17.00 | 0.35 | 98 | | | |
| 7 P-60-CH$_2$Br | | | | 16.1 | 0.7 | 96 |
| 8 P-60-CH$_2$Br —CO$_2$H | | | | 11.9 | 0.3 | 98 |

[1]Reactions were done in potassium phosphate pH 9.00, for 16 hours, and non-specifically bound oligonucleotides were removed by 3 washes with sodium pyrophosphate, followed by 3 washes with NaOH, pH 12.00.
[2]End attachment (%) = [(oligo-SH) − (oligo-PO4) ÷ oligo-SH The hybridization potential of oligonucleotides immobilized on P-60 supports (MW 60,000 cut-off) was evaluated using [$^{32}$P]-oligonucleotide-length target and a 7 kb DNA single-stranded plasmid in a sandwich format. The P-60 support was chosen for the study, since this matrix displayed the best attachment efficiencies in the coupling reaction with thiol-oligonucleotide derivatives. The results of the capture experiments are summarized in Table V.

As seen in the Table, both types of P-60 oligonucleotide supports proved to be better than Sephacryl™ dextran beads for direct capture of oligonucleotides. The support-bearing carboxyl functionalities on the surface displayed a non-specific binding identical to the Sephacryl™ dextran control and were marginally better than the P-60 hydrazide matrix. The polyacrylamide-based support showed a poorer ability than Sephacryl™ dextran beads to detect long target DNA in sandwich hybridizations and also displayed higher backgrounds. This result suggested that perhaps a substantial portion of the immobilized oligonucleotides was in the interior of the support, and therefore was not accessible to the long target fragment for hybridization. Consequently, only a small portion of the immobilized oligonucleotide would be available on the surface for the rate of duplex formation. At this stage, it was reasoned that it would be beneficial to reverse the functionalities in the coupling reaction. An impediment to obtaining better coupling efficiencies, and hence higher substitution levels, was the susceptibility of the thiol-oligonucleotide derivative to oxidation.

TABLE V

HYBRIDIZATION EXPERIMENTS WITH BROMOACETYL-DERIVATIZED POLYACRYLAMIDE SUPPORTS

| 86-31 immobilized support | Oligonucleotide Target | | | Sandwich with with 7 kb Target | | |
|---|---|---|---|---|---|---|
| | fmoles target | 86-32 (complementary) | 86-31 (non-complementary) | fmoles target | PHIV-1 (complementary) | PHIV-2 (complementary, |
| —CH$_2$Br P-60- —NHNH$_2$ | 0.5 | 89 | 0.2 | 0.5 | 8.3 | 0.85 |
| —CH$_2$Br P-60- —COOH | 0.5 | 74 | 0.15 | | | |
| Sephacryl™ dextran beads | 0.5 | 54 | 0.15 | 0.5 | 25 | 0.4 |

EXAMPLE 4

COVALENT ATTACHMENT OF BROMOACETYL-OLIGONUCLEOTIDES TO BIO-GEL™ POLYACRYLAMIDE-SH a. Preparation of sulfhydryl derivatives of Bio-gel™ supports One gram (wet weight) of Bio-Gel™ polyacrylamide hydrazide beads (500 μmoles-NHNH$_2$/dry gram) was equilibrated with 0.5M NaHCO$_3$, pH 9.7. To a suspension in 5 ml were added 30 mole equivalents (relative to NHNH$_2$ groups) of N-acetylhomocysteine thiolactone, and the mixture was shaken at room temperature overnight. The beads were washed with 300 ml 0.1M NaCl and stored in TE, pH 8.0, or 0.1M K$_2$HPO$_4$, pH 8.0. The reaction is illustrated in FIG. 1, reaction B. The level of sulfhydryl substitution was determined by titrating with 5,5'-dithiobis(2-nitrobenzoic acid) (DTNB) and monitoring the release of 3-carboxylato-4-nitrothiophenolate at 412 nm. The conversion was found to be dependent on the substitution level of hydrazide groups in the solid support, as illustrated in Table VI.

b. Glutarylation of sulfhydryl-Bio-Gel™ polyacrylamide beads

A one-gram sample of sulfhydryl Bio-Gel™ polyacrylamide was suspended in 20 ml 0.1M NaCl, and two 100-mg aliquots of glutaric anhydride were added at 15-minute intervals. The pH was maintained near 4.0 with 3M NaOH. After a total reaction time of 30 minutes, the beads were washed with 0.1M NaCl. Hydrolysis of thioesters was then carried out with 10 ml 0.1M Tris·HCl, pH 8.5, for 1 hour at room temperature.

TABLE VI

REACTION OF HYDRAZIDE SUPPORTS WITH N-ACETYLHOMOCYSTEINE LACTONE

| Type of support | µmole NHNH$_2$/ gm | molar excess thiol lactone | % NHNH$_2$ conversion | µmole SH/gm |
|---|---|---|---|---|
| 1 P-2-SH | 50 | 100 | 3.8 | 1.9 |
| 2 P-2-SH | 500 | 30 | 9.9 | 49.4 |
| 3 P-10-SH | 50 | 100 | 7.1 | 3.6 |
| 4 P-60-SH | 50 | 100 | 7.6 | 3.6 |
| 5 P-200-SH | 50 | 100 | 4.3 | 2.2 |
| 6 P-200-SH —SH[1] | 500 | 30 | 14.2 | 70.3 |
| 7 P-200 —CO$_2$H | 500 | 30 | 15.3 | 76.3 |
| 8 P-300-SH —SH[2] | 500 | 20 | 10.4 | 52.2 |
| 9 P-300 -TNPH —SH[3] | 500 | 20 | 10.0 | 50.2 |
| 10 P-300 —CO$_2$H | 500 | 20 | 9.2 | 45.9 |

[1]Conversion of hydrazide groups in P-200-SH support with glutaric anhydride.
[2]Conversion of hydrazide groups in P-300-SH support with trinitrophenyl sulfonate.
[3]Conversion of hydrazide groups in P-300-SH supports with glutaric anhydride.

Further conversion of the remaining hydrazide groups in the thiol supports with glutaric anhydride or trinitrobenzene sulfonate provided matrices with mixed functionalities (≈SH and ≈COOH, or ≈SH and ≈TNPH, respectively). No modification of the thiol groups was observed in these reactions (Table VI, compare 6 and 7, and 8–10). The rationale behind the syntheses of these mixed supports was to exploit the anionic or dipolar properties of the carboxyl or TNPH groups in reducing non-specific adsorption of negatively charged nucleic acids in hybridization reactions. A family of thiol-functionalized polyacrylamide supports, spanning a wide range of exclusion volumes, was thus prepared, having thiol substitution levels varying from 2–76 µmoles per gram of material.

c. Preparation of bromoacetyl derivatives of oligonucleotides

Figure 3:
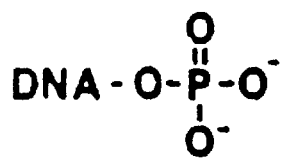
FIG. 3 is a reaction chart of the synthesis of bromoacetyl oligonucleotides.
Figure 3:
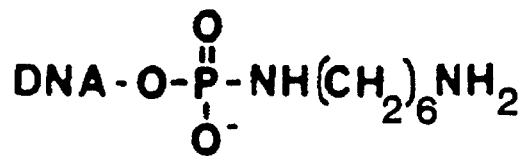
Figure 3:
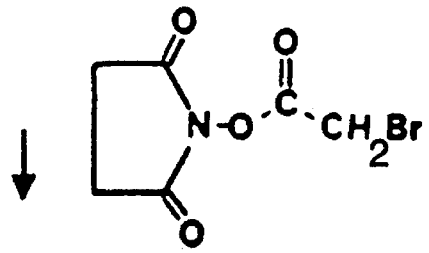
Figure 3:
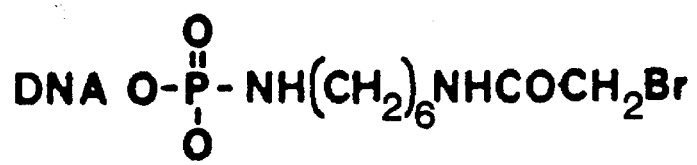
Figure 4:
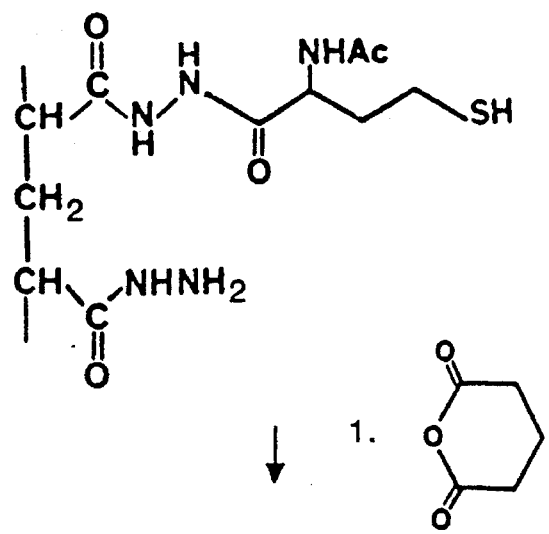
FIG. 4 shows the acylation of thiol-derivatized Bio-Gel™ polyacrylamide supports and the use of the polyacrylamide matrices with mixed functionalities in coupling with bromoacetyl oligonucleotides.
Figure 4:
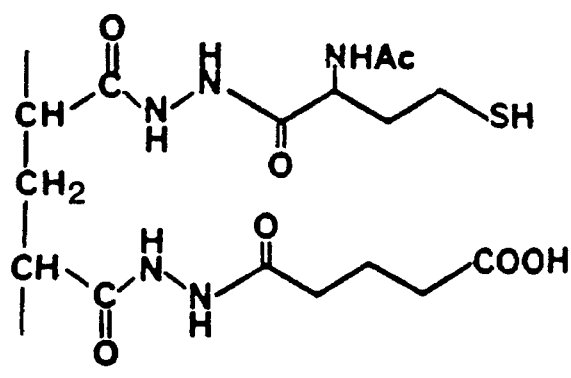
Figure 4:
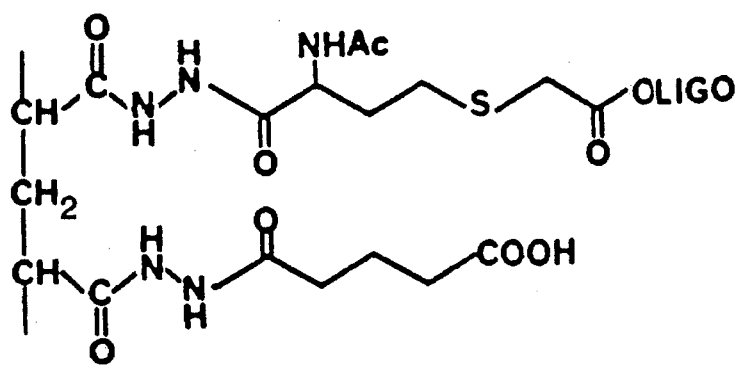

A 5'-phosphorylated oligonucleotide in a silanized Eppendorf tube was treated with 300 µl of 0.25M hexanediamine HCl, 0.1M methylimidazole, 0.15M EDC, pH 6.0, at room temperature for 20 hours. The amine derivative was precipitated twice with EtOH/LiCl and redissolved in 285 µl of 0.2M HEPES, pH 7.7. A 15-µl aliquot of a 10-mg/ml solution of N-succinimidyl bromoacetate in DMF was added. After a reaction time of 1 hour, the oligonucleotide was precipitated twice with EtOH/LiCl. The reaction is illustrated in FIG. 3. The overall phosphate-to-bromoacetamide transformation was estimated to be 60–70% by polyacrylamide gel analysis of [$^{32}$P]-labeled products, and susceptibility to cleavage of the 5'$^{32}$PO$_4$ group (unreacted phosphorylated oligonucleotide) by alkaline phosphatase treatment.

d. Covalent attachment of 5'-bromoacetyl-derivatized oligonucleotides to sulfhydryl-Bio-Gel™ polyacrylamide beads Sulfhydryl-Bio-Gel™ polyacrylamide support (1 gram wet weight) was reduced with 5 ml 20 mM DTT in 0.05M K$_2$HPO$_4$, pH 8.0, for 1 hour, then washed with 2 x 40 ml 0.05M K$_2$HPO$_4$, pH 8.0, followed by 2 x 40 ml 0.1M triethylammonium phosphate, 1 mM EDTA, pH 9.0. Five hundred pmoles of bromoacetyl-derivatized oligonucleotide was dissolved in 1 ml TEAP, EDTA, pH 9.0, and added to the resin in a 5-ml polypropylene tube. After purging the tube with N$_2$ and sealing with parafilm, the bead sample was agitated on a rotary mixer overnight. The beads were washed with: (a) 3 x 10 ml 0.1M Na$_2$P$_2$O$_7$, pH 7.5, and (b) 2 x 10 ml TE, pH 8.0. Unreacted sulfhydryl groups were capped by reducing the support with 3 ml 20 mM DTT in 0.05M K$_2$HPO$_4$, pH 8.0, for 30 minutes. After removal of excess DTT and equilibration in 0.1M TEAP, 1 mM EDTA, pH 9.0, 3 ml of 5 mM iodoacetic acid in the same buffer was added and allowed to react for 1 hour. After filtration of unreacted reagent through a sintered glass funnel (porosity C), the bead samples were stored in TE, pH 8.0, at 4° C.

e. Coupling efficiencies of bromoacetyl oligonucleotides to thiol polyacrylamide supports The immobilization studies concentrated on P-2, P-200, and P-300 matrices, because of their vastly different exclusion volumes. It was hypothesized that the highly cross-linked P-2 support (MW cut-off 2,000) would have all the oligonucleotides attached on the surface, and hence be available for capture. The small pore size would also prevent the inclusion of nucleic acids during the hybridization and thereby be beneficial in reducing non-specific binding. In contrast, the P-200 and P-300 supports (MW cut-off 200,00 and 300,000) are closer to Sephacryl™ dextran (MW cut-off 20,000,000) in structural features in having large pores in the matrix. The results of the coupling reaction (see FIG. 4) of these derivatives with 2O these thiol-polyacrylamide supports are shown in Table VII.

TABLE VII

COUPLING YIELDS OF TRIOL SUPPORTS WITH BROMOACETYL OLIGONUCLEOTIDES

| Support (500 µmole NHNH$_2$ initial substitution time) | 86-31-CH$_2$Br % attached | 86-31-PO$_4$ % attached | % end attached |
|---|---|---|---|
| 1 P-2-SH | 3.5 | 0.2 | 94 |
| 2 P-200-SH —SH | 28.6 | 0.5 | 98 |
| 3 P-200 -TNPH | 29.3 | 0.5 | 98 |
| 4 P-300-SH —SH | 29.9 | 1.7 | 94 |
| 5 P-300 —CO$_2$H | 22 | 0.5 | 98 |

The coupling with the P-2 support proceeded in low yields, even though the thiol concentration on the matrix greatly exceeded the oligonucleotide concentration in the reaction. P-200 and P-300 supports provided satisfactory yields and, in contrast to the reverse format, were consistently reproducible. As was noted earlier, the actual yields are higher than the values reported, due to the incomplete conversion of 5'-phosphorylated oligonucleotides to their bromoacetyl derivatives. The other factors to note are: (1) additional functionalization of the thiol supports with COOH or TNPH groups does not have a significant effect on the attachment efficiencies (entries 2 and 3, and 4 and 5); (2) the reaction with bromoacetyl oligonucleotides results in end-attachment of the nucleic acid to the support, as evidenced by the minimal binding of the phosphorylated oligonucleotide control; (3) a comparison of the reactivity of bromoacetyl oligonucleotides with P-200 thiol supports indicated that the displacement of bromide by the thiol groups on the support was 30% more efficient than addition to the 5'-maleimide-derivatized oligonucleotide; and (4) the optimum pH for coupling was determined to be pH 9.0; higher coupling efficiencies are obtained using triethylammonium phosphate as the coupling buffer, compared to potassium phosphate.

f. Hybridization characteristics of thiol supports

The hybridization of oligonucleotides on polyacrylamide thiol supports was tested by direct capture of oligonucleotide targets and in a sandwich format with TAS-generated RNA transcripts. Two sets of experiments are summarized in Table VIII.A., which compares P-2 and P-200 supports with Sephacryl™ dextran beads.

wich hybridization to a 7 kb target fragment (Table VIII.B). While the polyacrylamide support was clearly superior to Sephacryl™ dextran in oligonucleotide capture, it showed not only a lower efficiency in sandwich capture of the long target, but also an unexpected increase in non-specific binding.

To address the non-specific adsorption problem, the polyacrylamide supports (P-200 and P-300) were treated with gluteric anhydride and/or iodoacetic acid to convert the hydrazide and sulfhydryl functionalities to carboxylic groups. The hybridization results with these modified supports are shown in Table VIII.C. Consistent with other observations, the direct capture of oligonucleotides by all of the polyacrylamide supports was superior to Sephacryl™ dextran beads. While similar levels of sandwich capture of the TAS transcripts were exhibited by both the polyacrylamide and Sephacryl™ dextran supports, the problem of non-specific adsorption surfaced again for the thiol-based supports. Capping the hydrazide and thiol groups on the support helped to reduce the background 3- to 5-fold (Table VIII.C, entries 2 and 3).

TABLE VIII

HYBRIDIZATION STUDIES WITH TRIOL SUPPORTS

| | Oligonucleotide (direct capture) | | | TAS (sandwich) | | | 7 kb target (sandwich) | | |
|---|---|---|---|---|---|---|---|---|---|
| | Target (fmoles) | 86-32 (comp) | 86-31 (non-comp) | Target (fmoles) | comp | non-comp | Target (fmoles) | comp | non-comp |
| A. 86-31 Immobilized Support | | | | | | | | | |
| 1 P-2-SH —NHNH$_2$ | 3.75 | 70.9 | 0.13 | 0.5 | 2.9 | 1.4 | | | |
| 2 P-200-SCH$_2$COOH —NHNH$_2$ | 3.75 | 91.9 | 0.35 | 0.5 | 8.6 | 1.9 | | | |
| 3 Sephacryl™ dextran beads | 3.75 | 77.7 | 0.25 | 0.5 | 12.0 | 0.85 | | | |
| B. | | | | | | | | | |
| 1 P-200-SH —NHNH$_2$ | 0.5 | 82 | 0.6 | | | | 0.5 | 13 | 1.9 |
| 2 Sephacryl™ dextran beads | 0.5 | 61 | 0.2 | | | | 0.5 | 35 | 0.3 |
| C. | | | | | | | | | |
| 1 P-300-SCH$_2$CO$_2$H —NHNH$_2$ | 3.75 | 88.4 | 0.56 | 0.5 | 24 | 7 | | | |
| 2 P-200-SH —NHNH$_2$CO$_2$H | 3.75 | 87.8 | 0.55 | 0.5 | 17 | 4 | | | |
| 3 P-300-SCH$_2$CO$_2$H —NHNH$_2$CO$_2$H | 3.75 | 74.5 | 0.58 | 0.5 | 15 | 2 | | | |
| 4 Sephacryl™ dextran beads | 3.75 | 66.5 | 0.18 | 0.5 | 13 | 0.6 | | | |

Both types of polyacrylamide supports compared very favorably with Sephacryl™ dextran beads in showing excellent ability to capture target oligonucleotides and low non-specific binding. In sandwich hybridizations with TAS products, however, the P-2 support displayed a reduced ability to capture target, as well as a high background. Although the P-200 support was better than P-2 in sandwich hybridizations, it suffered in comparison to Sephacryl™ dextran beads due to its 2-fold higher non-specific binding. This feature was again seen in a set of experiments comparing Sephacryl™ dextran beads with P-200 supports in a sand- In direct capture experiments with 3.75 fmoles of target oligonucleotide, non-specific binding was observed to be ≈0.55% for all three types of polyacrylamide supports (Table VIII.C, entries 1, 2, and 3). In sandwich hybridizations in which 5 fmoles of detection oligonucleotide were used, a 5- to 14-fold increase of non-specific binding was noted.

In order to test the premise that the long target was not captured as efficiently, and perhaps had a role to play in these increase of non-specific binding, direct capture of a labeled PCR product by polyacrylamide and Sephacryl™ dextran beads was investigated. Table IX summarizes the results of the experiment.

TABLE IX

DIRECT CAPTURE OF PCR-AMPLIFIED, DOUBLE-STRANDED PRODUCT

| 86-31 immobilized support | Target (fmole) | Complementary (% capture) | Non-complementary (% capture) | Signal/ noise |
|---|---|---|---|---|
| P-300-SH | 1 | 11 | 1.1 | 10 |
| P-300-SH —$CO_2H$ | 1 | 19.5 | 0.75 | 26 |
| P-200-SH —$CO_2H$ | 1 | 23 | 1.7 | 13.5 |
| Sephacryl™ | 1 | 13.5 | 0.4 | 33.8 |
| dextran beads | 1 | 17.5 | 0.65 | 26.9 |

1. Average of duplicates of two separate experiments

As seen in the Table, both carboxylated forms of the polyacrylamide supports showed better capture efficiencies of the long-stranded DNA target than Sephacryl™ dextran beads, while the backgrounds were 2- to 3-fold higher than Sephacryl™ dextran. These results with long target DNA closely paralleled the results with oligonucleotide targets (Table VIII.C.). Thus, it appears that while the polyacrylamide supports can capture long targets as efficiently as (if not better than) Sephacryl™ dextran beads, there are some other, at present unknown, factors involved in sandwich hybridizations which contribute to the increase of non-specific binding.

g. Hybridization of supports with oligonucleotide-enzyme conjugates

The direct capture and background properties of the polyacrylamide support were also tested with oligonucleotide-alkaline phosphatase conjugates. The supports were incubated with complementary oligonucleotide-enzyme conjugates for 1 hour and then subjected to the standard washes to remove unbound conjugate. Color development was allowed to proceed for 1 hour using p-nitrophenyl phosphate as substrate, and the release of p-nitrophenolate was determined spectrophotometrically. A non-complementary oligonucleotide-enzyme conjugate was used as a control. Data from this study are summarized in Table X.

The following observations can be made from the results. Although the capture of oligonucleotides polyacrylamide supports are more efficient than Sephacryl™ dextran beads in the direct capture of oligonucleotides, the average signal generated by hydrolysis of the substrate by Sephacryl™ dextran bead-bound conjugates was ≈40% higher than hydrolysis of the substrate by polyacrylamide support-bound conjugates. Since, the average of the backgrounds for both supports was nearly identical, the difference in hydrolysis accounted for the superior signal-to-noise ratio of Sephacryl™ dextran beads compared to the polyacrylamide supports.

In order to determine whether the presence of the immobilized oligonucleotide on the support contributed in some manner to non-specific binding, oligonucleotide-bound support was comixed with oligonucleotide-free support in a 1:9 w/w ratio. As seen in Table X, entries 3 and 5, no significant conclusions can be made from the signal-to-noise ratios.

TABLE X

DIRECT CAPTURE OF OLIGONUCLEOTIDE-ENZYME CONJUGATES BY POLYACRYLAMIDE SUPPORTS

| 86-31 Immobilized[3] Support | fmoles | 86-32-AP (complementary) | 86-31-AP (non-complementary) | Signal/ noise (S/N) | Average S/N |
|---|---|---|---|---|---|
| 1 P-200-SH ⁻$CO_2H$ | 35 | .242 | .030 | 8.5 | 8.5 |
| 2 P-200-SCH$_2$CO$_2$H ⁻$CO_2H$ | 35 | .143 | .006 | 21.8 | 14.6 |
|  | 35 | .239 | .031 | 7.4 |  |
| 3 10% P-200-SCH$_2$CO$_2$H[4] ⁻$CO_2H$ | 35 | .135 | .002 | 61.8 | 36.47 |
|  | 35 | .172 | .015 | 11.0 |  |
| 4 P-300-SCH$_2$CO$_2$H ⁻$CO_2H$ | 35 | .216 | .019 | 12 |  |
|  | 35 | .173 | .010 | 15.8 |  |

| 86-31 immobilized[1] Support | fmoles | 86-32-AP (complementary) | 86-31-AP (non-complementary) | Signal/ noise (S/N) | Average S/N |
|---|---|---|---|---|---|
|  | 35 | .222 | .025 | 8.5 | 12.1 |
| 5 10% P-300-SCH$_2$CO$_2$H ⁻$CO_2H$ | 35 | .141 | .009 | 14.3 |  |
|  | 35 | .190 | .026 | 7.0 | 10.7 |
| 6 Sephacryl™ dextran beads | 35 | .294 | .013 | 23.9 | 19.6 |
|  | 35 | .238 | .015 | 15.3 |  |

[3]Absorbances at 410 nm of p-nitrophenolate released from hydrolysis of 2-nitrophenyl phosphate by support-bound conjugates are reported. The values reported are an average of duplicate experiments. Each row represents a different experiment performed with a duplicate set of solid supports (50 mg).
[4]Oligonucleotide-immobilized solid support was mixed with polyacrylamide support possessing carboxyl functionalities only.

EXAMPLE 5

COVALENT ATTACHMENT OF BROMOACETYL OLIGONUCLEOTIDES TO TRISACRYL™ POLYACRYLAMIDE-SH a. Preparation of amine derivatives of Trisacryl™ polyacrylamide A 20-ml suspension of Trisacryl™ polyacrylamide GF-2000 (IBF, Biotechnics, USA) was pipetted into a sintered glass funnel, washed with 200 ml H₂O, and sucked dry for 10 minutes. The dried sample (≈11 grams) was added slowly to 20 ml of distilled ethylene diamine equilibrated at 90° C. in an oil bath. After one hour, the reaction mixture was cooled by the addition of 30 ml of crushed ice. Excess ethylene diamine was removed by washing the resin with 400 ml 0.2M NaCl, 0.001M HCl, followed by 500 ml 0.1M NaCl in a funnel. Washing was continued until the filtrate gave a negative test with TNBS reagent (Example 1d).

b. Preparation of sulfhydryl derivative of Trisacryl™ polyacrylamide

Figure 5:
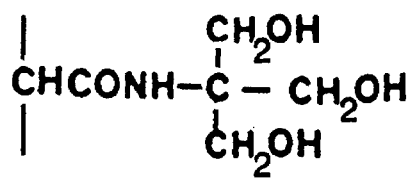
FIG. 5 is a synthetic scheme for the preparation of Trisacryl™ polyacrylamide-SH supports.
Figure 5:
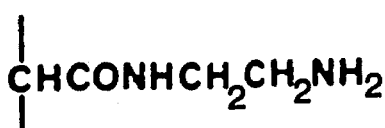
Figure 5:
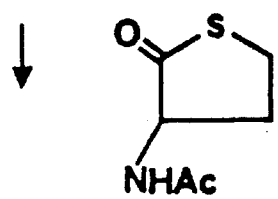
Figure 5:
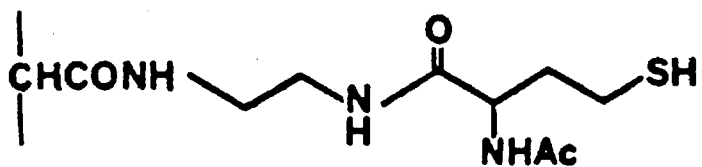
Figure 5:
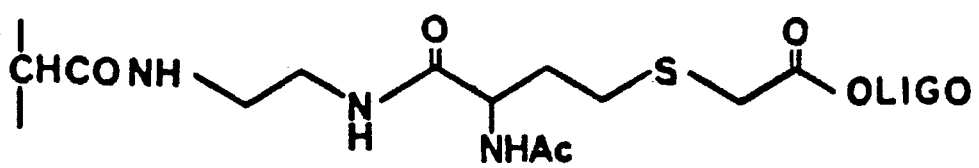

The Trisacryl™ polyacrylamide-amine support was equilibrated with 0.5M NaHCO₃, pH 9.7, and the volume was adjusted to 30 ml in a 50-ml Sarstedt conical tube. Solid N-acetyl homocysteine lactone (1 gram) was added, and the tube was shaken at room temperature for 2 hours. Then, another 1 gram of reagent was added, and the sample was shaken overnight. The beads were washed with 500 ml of 0.1M NaCl, and the sulfhydryl group concentration was estimated by titrating with Ellman's reagent (DTNB) (Example 1e). The reaction is illustrated in FIG. 5.

Titration of the sulfhydryl groups on the Trisacryl™ polyacrylamide-SH support indicated a substitution level of 12.3 μmoles-SH per wet gram of resin.

c. Succinylation of sulfhydryl-Trisacryl™-polyacrylamide

A 2-gram sample of Trisacryl™ polyacrylamide-SH was equilibrated in 20 ml 0.1M NaOAc, pH 6.0, and treated with 100 mg solid succinic anhydride. After shaking for 30 minutes, another 100 mg of anhydride was added to the suspension and shaken for a further 30 minutes. The beads were then equilibrated in 40 ml 0.1M Tris, pH 8.5. After 1 hour, the support was washed with TE, pH 8.0, and stored at 4° C.

d. Covalent attachment of 5'-bromoacetyl-derivatized oligonucleotides to sulfhydryl-Trisacryl™-polyacrylamide The solid support (1 gram) was reduced with DTT following the procedure used for Bio-Gel™ polyacrylamide beads (Example 2d) and equilibrated in 0.1M TEAP, 1Mm EDTA, pH 9.0. Five hundred pmoles of bromoacetyl-derivatized oligonucleotide dissolved in 1 ml TEAP/EDTA were added to the support, and the tube was purged with N₂ and sealed. After overnight agitation on a rotary mixer, 100 μmoles of iodoacetic acid were added and the mixture was left at room temperature for 1 hour. The beads were washed with 4 x 20 ml 0.1M Na₂P₂O₇, pH 7.5, followed by 2 x 20 ml TE, pH 8.0.

The reaction is illustrated in FIG. 6. The coupling reaction with [³²P]-labeled, bromoacetylated oligonucleotides resulted in 12% of the label being attached to the sulfhydryl support, and the level of end-attachment was determined to be 97%. The actual coupling yield for this reaction was estimated to be approximately 20%, based on a purity of 60–70% for the bromoacetyl oligonucleotide. Although the coupling yield was lower than those obtained with the Bio-Gel™ polyacrylamide supports (40–45%), the Trisacryl™ polyacrylamide-resin still contained a huge excess of oligonucleotide molecules relative to the amounts of target (0.5–5 fmoles) used in the hybridization experiments.

e. Hybridization characteristics of sulfhydryl-Trisacryl™ polyacrylamide supports The initial hybridization study (Table XI.A) involving direct capture of 3.75 fmoles of [³²P]-labeled target with Trisacryl™ polyacrylamide-SH (containing oligo 86-31) showed that the non-specific binding of non-complementary target was about three times higher than for the Sephacryl™ dextran beads support (0.42% vs. 0.14%).

Alkylation of the unreacted sulfhydryl groups on the Trisacryl™ polyacrylamide support with iodoacetate reduced the non-specific binding by increasing the negative charge-density of the matrix. When the alkylated Trisacryl™ polyacrylamide support was assayed in a direct capture experiment, the non-specific binding dropped considerably to 0.15%, which was comparable to that obtained with Sephacryl™ dextran beads.

The results from a TAS sandwich experiment (Table XI.B) using 0.5 fmoles of target RNA evidence the superiority of Trisacryl™ polyacrylamide over Sephacryl™ dextran beads when linked to oligonucleotides as described herein. This is demonstrated by the higher percent capture of complementary target. The Trisacryl™ polyacrylamide support also exhibited extremely low non-specific background in contrast to the higher background of Bio-Gel™ polyacrylamide supports, which had been the principal contributor to the lower signal/noise ratios in the TAS sandwich format.

TABLE XI

HYBRIDIZATION STUDIES WITH
Trisacryl ™ polyacrylamide-SH

A. Direct Capture (% Oligo Bound)

| 86-31 Support | Target (fmoles) | 86-32 (Comp.) | 86-31 (Non-Comp) | Signal/ Noise |
|---|---|---|---|---|
| Trisacryl ™ polyacrylamide-SH | 375 | 66.5 | 0.42 | 158.3 |
| Trisacryl ™ polyacrylamide-SH (ICH₂OOH-treated) | 375 | 69.8 | 0.15 | 465.3 |
| Sephacryl ™ dextran beads | 375 | 54.6 | 0.14 | 390.0 |

B. TAB HIV RNA (SANDWICH) CAPTURE

| 86-31 Support | Target (fmoles) | 86-32 (Comp.) | 86-31 (Non-Comp) | Signal/ Noise |
|---|---|---|---|---|
| Trisacryl ™ polyacrylamide-SH (ICH₂OOH-treated) | 0.5 | 17.0 | 0.1 | 170.0 |
| Sephacryl ™ dextran beads | 0.5 | 12.5 | 0.9 | 13.9 |

C. Direct Capture of Oligonucleotide-enzyme Conjugates

| 86-31 Support | Target (fmoles) | 86-32 (Comp.) | 86-31 (Non-Comp) | Signal/ Noise |
|---|---|---|---|---|
| Trisacryl ™ polyacrylamide-SH (ICH₂OOH-treated) | 5 | 0.179 | 0.003 | 61.7 |
| Sephacryl ™ dextran beads | 5 | 0.319 | 0.023 | 14.4 |

Finally, the Trisacryl™ polyacrylamide support was tested with oligonucleotide-alkaline phosphatase conjugates to determine the level of direct capture and background properties (Table XI.C.). Incubation of complementary and non-complementary conjugates with Trisacryl™ polyacrylamide and Sephacryl™ dextran beads followed by standard washing procedures and a colorimetric assay using p-nitrophenyl phosphate was performed with 5 fmoles of conjugates. Although the capture of complementary target was higher in the case of Sephacryl™ dextran beads, the non-specific binding of the Trisacryl™ polyacrylamide was considerably lower, resulting in a 4-fold improvement in signal-to-noise compared to Sephacryl™ dextran beads.

EXAMPLE 6

COVALENT ATTACHMENT OF BROMOACETYL OLIGONUCLEOTIDES TO TRISACRYL™ POLYACRYLAMIDE-SH

The following oligonucleotide sequences were attached to Trisacryl™ polyacrylamide-SH using the same general procedures as described in Example 5:
Sequence ID No. 3: 5' AGTCTAGCAGAAGAAGAGG-TAGTAATTAGA 3' (86-273),
Sequence ID No. 4: 5' AGTCTAGATTGGTAATAACAA-CATATT 3' (87-083),
Sequence ID No. 5: 5' AGAACTCAAGACTTCTGG-GAAGTTC 3' (89-419),
Sequence ID No. 6: 5' AGGATCTGACTTAGAAAT-AGGGCAGCA 3' (89-534),
Sequence ID No. 7: 5' ATGGGTTATGAACTCCATCCT-GATAAATGG 3' (89-535),
Sequence ID No. 8: 5' GTTCCGCCCTTCCTGAAGT-GCCC 3' (92-159), and
Sequence ID No. 9: 5' GTTCCGCCCTTCCTGAAGTGC-CCTTATTG 3' (92-189).

EXAMPLE 7

COMPARISON OF SANDWICH HYBRIDIZATION CAPTURE OF RNA TRANSCRIPTS ON TRISACRYL™ POLYACRYLAMIDE AND SEPHACRYL™ DEXTRAN SUPPORTS

Both Trisacryl™ polyacrylamide and Sephacryl™ dextran supports were labeled with oligonucleotides using essentially the same procedures as Example 5. The sandwich hybridization of TAS-generated RNA transcripts on the two supports were compared. Total RNA was extracted from HIV-1-infected CEM cells and a region of the vif gene was amplified by the TAS procedure using primers 88-77 and 86-29. The TAS primer sequences were:
Sequence ID No. 10: 5' AATTTAATACGACTCACTAT-AGGGACACCTAGGGCTAACTATGTGTC-CTAATAAGG 3' (88-77); and
Sequence ID No. 11: 5' ACACCATATGTATGTTTCAGG-GAAAGCTA 3' (86-29).
The TAS products were quantitated by slot-blot comparison with known concentration of pARV7A/2 plasmid. The TAS products were diluted in TE and sandwich hybridization was carried out using 50–1000 attomoles of target and maintaining a 10:1 ration of detection probe to target. The detection probe sequence was 86-31 and the capture sequence on the solid supports was 87-83. A non-complementary TAS product (50–1000 attomoles) was used to estimate the non-specific binding and signal to noise was expressed as the ration of $^{32}P$ counts obtained with complementary and non-complementary TAS products. The results obtained are presented in Table XII.

TABLE XII

| SANDWICH HYBRIDIZATION STUDIES | | |
|---|---|---|
| | Signal to Noise | |
| Target RNA (fmole) | Trisacryl™ Polyacrylamide Support | Sephacryl™ Dextran Support |
| 0.05 | 9 | 3 |
| 0.1 | 15 | 4 |
| 0.25 | 25 | 6 |
| 0.5 | 60 | 7 |
| 1.0 | 72 | 11 |

As can be seen in Table XII, the Trisacryl™ polyacrylamide supports provide a significant improvement in sensitivity as compared to the Sephacryl™ dextran supports.

EXAMPLE 8

LEVEL OF ATTACHMENT OF OLIGONUCLEOTIDE TO TRISACRYL™ POLYACRYLAMIDE SUPPORTS

Using the same procedures as in Example 5, varying amounts of bromoacetyl oligonucleotide (92-189) were coupled to with a fixed amount (10 g) of Trisacryl™ polyacrylamide-SH beads. The amount of oligonucleotide attachment was determined by direct capture experiments using a labeled oligonucleotide complementary to oligonucleotide 92-189. The following results were obtained:

TABLE XIII

| LEVEL OF ATTACHMENT | |
|---|---|
| Bromoacetyl Oligonucleotide Added (nmoles/g) | Oligonucleotide Attached (nmoles/g) |
| 0.8 | 0.052 |
| 1.6 | 0.08 |
| 3.2 | 0.156 |
| 6.4 | 0.196 |

Increasing the amount of added reactive carbon center-derivatized oligonucleotide significantly increases the level of attachment to the thiol-derivatized polyacrylamide support.

Since modifications will be apparent to those of skill in the art, it is intended that this invention be limited only by the scope of the appended claims.

That which is claimed is:

1. A polyacrylamide support to which RNA or DNA oligonucleotides are covalently attached via a thioether linkage, wherein:

at least about 60% of the oligonucleotides are linked to the polyacrylamide support at the 5'-end of the oligonucleotides;

the polyacrylamide supports include repeating units with carboxamide side groups of the formula:

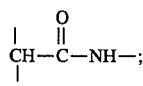

the polyacrylamide support has a molecular weight exclusion limit of greater than about 2000 daltons; and the polyacrylamide support with attached oligonucleotides is selected from the group consisting of the supports of formulae:

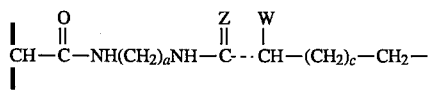

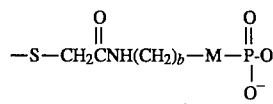

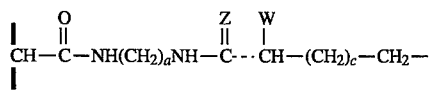

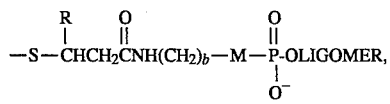

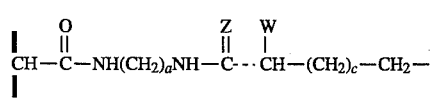

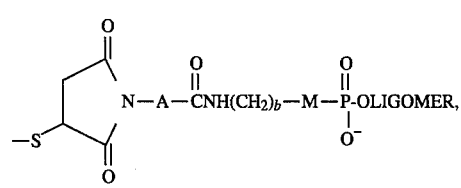

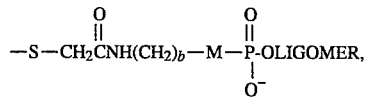

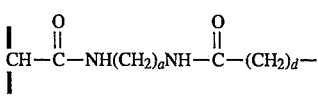

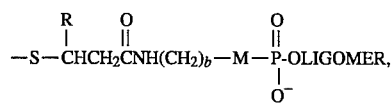

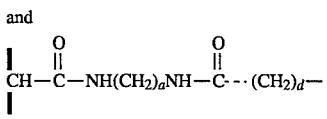

and

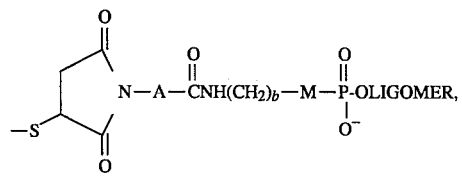

in which:

M is —NH— or oxygen;

R is independently hydrogen or an alkyl group containing 1 to 6 carbon atoms;

a is 0 or 2 to 20;

b is 0 or 2 to 20 when M is —NH— or b is 0 to 20;

c is 1 or 2;

d is 2 to 6;

A is a linking group selected from the group consisting of —(CHR)$_m$—, —C$_6$H—, —C$_6$H$_{10}$—, —(CHR)$_m$C$_6$H$_{10}$—, and —C$_6$H$_{10}$(CHR)$_m$— where m is an integer equal to 1 to 20;

W is hydrogen or —NHC(=O)—R' where R' is an alkyl group having 1 to 6 carbon atoms; and Z is oxygen or NH$_2^+$.

2. A polyacrylamide support as defined in claim 1, wherein at least about 90% of the oligonucleotides are linked to the polyacrylamide support at the 5'-end of the oligonucleotides and the polyacrylamide support has a molecular weight exclusion limit of greater than about 400,000 daltons.

3. A polyacrylamide support as defined in claim 2, wherein at least about 95% of the oligonucleotides are linked to the polyacrylamide support at the 5'-end of the oligonucleotides and the polyacrylamide support has a molecular weight exclusion limit of greater than about 2×10$^7$ daltons.

4. A polyacrylamide support as defined in claim 3, wherein the polyacrylamide support with attached oligonucleotides has the formula $$\overset{|}{\underset{|}{CH}}-\overset{O}{\overset{\|}{C}}-NH(CH_2)_aNH-\overset{Z}{\overset{\|}{C}}\cdots \overset{W}{\overset{|}{CH}}-(CH_2)_c-CH_2-S-CH_2CNH(CH_2)_b-M-\overset{O}{\underset{O^-}{\overset{\|}{P}}}-OLIGOMER,$$

wherein

M is —NH— or oxygen;

b is 0 or 2 to 6 (when M is —NH—) and b is 0 to 6 (when M is —O—);

c is 1;

W is hydrogen or —NHC(=O)—R' where R' is an alkyl group having 1 to 6 carbon atoms; and Z is oxygen.

5. A polyacrylamide support as defined in claim 3, wherein the polyacrylamide support with attached oligonucleotides has the formula $$\overset{|}{\underset{|}{CH}}-\overset{O}{\overset{\|}{C}}-NH(CH_2)_aNH-\overset{Z}{\overset{\|}{C}}\cdots \overset{W}{\overset{|}{CH}}-(CH_2)_c-CH_2-S-\overset{R}{\overset{|}{CH}}CH_2\overset{O}{\overset{\|}{C}}NH(CH_2)_b-M-\overset{O}{\underset{O^-}{\overset{\|}{P}}}-OLIGOMER,$$

wherein

M is —NH— or oxygen;

R is hydrogen or an alkyl group containing 1 to 6 carbon atoms;

a is 0 or 2 to 6;

b is 0 or 2 to 6 (when M is —NH—) and b is 0 to 6 (when M is —O—);

c is 1;

W is hydrogen or —NHC(=O)—R' where R' is an alkyl group having 1 to 6 carbon atoms; and Z is oxygen.

6. A polyacrylamide support as defined in claim 3, wherein the polyacrylamide support with attached oligonucleotides has the formula $$\overset{|}{\underset{|}{CH}}-\overset{O}{\overset{\|}{C}}-NH(CH_2)_aNH-\overset{Z}{\overset{\|}{C}}\cdots \overset{W}{\overset{|}{CH}}-(CH_2)_c-CH_2-S\overset{\overset{O}{\|}}{\underset{\underset{O}{\|}}{\diagdown}}N-A-\overset{O}{\overset{\|}{C}}NH(CH_2)_b-M-\overset{O}{\underset{O^-}{\overset{\|}{P}}}-OLIGOMER,$$

wherein

M is —NH— or oxygen;

a is 0 or 2 to 6;

b is 0 or 2 to 6 when M is —NH— or b is 0 to 6 (when M is —O—);

c is 1;

A is a linking group selected from the group consisting of —(CHR)$_m$—, —C$_6$H$_4$—, —C$_6$H$_{10}$—, —(CHR)$_m$C$_6$H$_{10}$—, and —C$_6$H$_{10}$(CHR)$_m$— where m is an integer equal to 1 to 6 and R is hydrogen or an alkyl group containing 1 to 6 carbon atoms;

W is hydrogen or —NHC(=O)—R' where R' is an alkyl group having 1 to 6 carbon atoms; and Z is oxygen.

7. A polyacrylamide support as defined in claim 3, wherein the polyacrylamide support with attached oligonucleotides has the formula $$\overset{|}{\underset{|}{CH}}-\overset{O}{\overset{\|}{C}}-NH(CH_2)_aNH-\overset{O}{\overset{\|}{C}}-(CH_2)_d-S-CH_2\overset{O}{\overset{\|}{C}}NH(CH_2)_b-M-\overset{O}{\underset{O^-}{\overset{\|}{P}}}-OLIGOMER,$$

wherein

M is —NH— or oxygen;

a is 0 or 2 to 6;

b is 0 or 2 to 6 (when M is —NH—) and b is 0 to 6 (when M is —O—); and d is 2 to 6.

8. A polyacrylamide support as defined in claim 3, wherein the polyacrylamide support with attached oligonucleotides has the formula

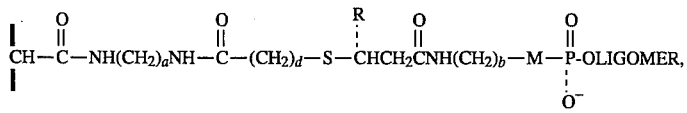

wherein

M is —NH— or oxygen;

R is hydrogen or an alkyl group containing 1 to 6 carbon atoms;

a is 0 or 2 to 6;

b is 0 or 2 to 6 (when M is —NH—) and b is 0 to 6 (when M is —O—); and d is 2 to 6.

9. A polyacrylamide support as defined in claim 3, wherein the polyacrylamide support with attached oligonucleotides has the formula

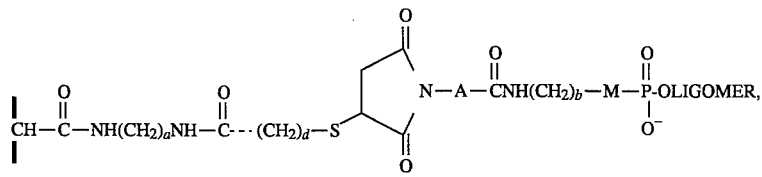

wherein

M is —NH— or oxygen;

a is 0 or 2 to 6;

b is 0 or 2 to 6 when M is —NH— or b is 0 to 6 when M is —O—;

d is 2 to 6; and

A is a linking group selected from the group consisting of —(CHR)$_m$—, —C$_6$H$_4$—, —C$_6$H$_{10}$—, —(CHR)$_m$C$_6$H$_{10}$—, and —C$_6$H$_{10}$(CHR)$_m$— where m is an integer equal to 1 to 6 and R is hydrogen or an alkyl group containing 1 to 6 carbon atoms.

10. A polyacrylamide support to which RNA or DNA oligonucleotides are covalently attached via a thioether linkage, wherein at least about 60% of the oligonucleotides are linked to the polyacrylamide support at the 5'-end of the oligonucleotides;

the polyacrylamide supports include repeating units with carboxamide side groups of the formula:

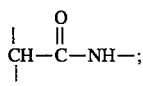

the polyacrylamide support has a molecular weight exclusion limit of greater than about 2000 daltons; and the polyacrylamide support with attached oligonucleotides is selected from the group consisting of the formulae:

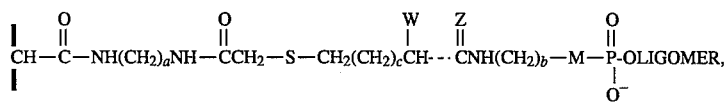

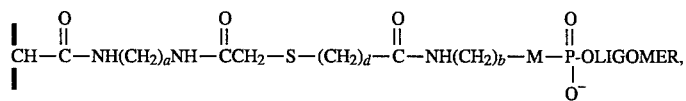

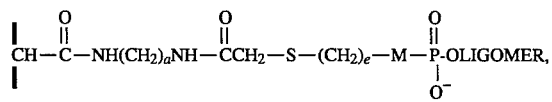

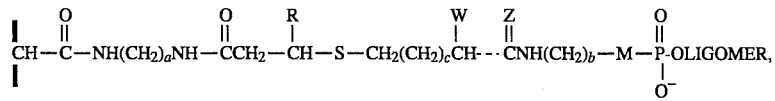

-continued

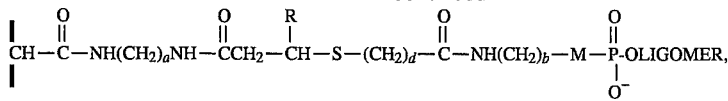

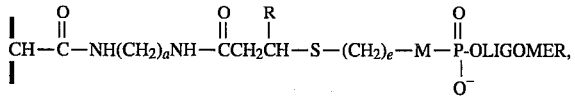

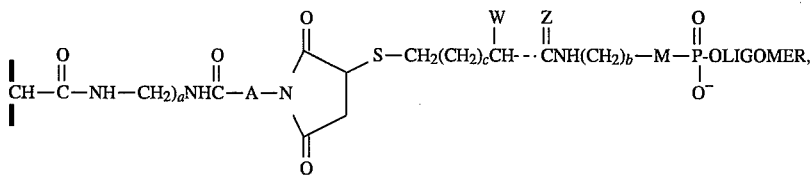

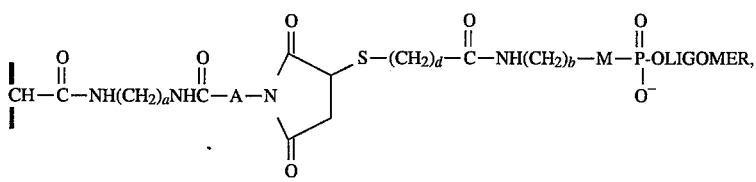

and

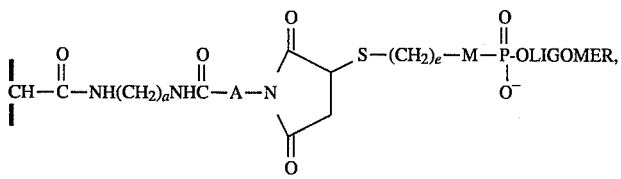

wherein

M is —NH— or oxygen;

R is independently hydrogen or an alkyl group containing 1 to 6 carbon atoms;

a is 0 or 2 to 20;

b is 0 or 2 to 20 when M is —NH— or b is 0 to 20 when M is —O—;

c is 1 or 2;

d is 2 to 6;

e is 2 to 20;

A is a linking group selected from the group consisting of —(CHR)$_m$—, —C$_6$H$_4$—, —C$_6$H$_{10}$—, —(CHR)$_m$C$_6$H$_{10}$—, and —C$_6$H$_{10}$(CHR)$_m$— where m is an integer equal to 1 to 20;

W is hydrogen or —NHC(=O)—R' where R' is an alkyl group having 1 to 6 carbon atoms; and Z is oxygen or NH$_2^+$.

11. A polyacrylamide support as defined in claim 10, wherein at least about 90% of the oligonucleotides are linked to the polyacrylamide support at the 5'-end of the oligonucleotide and the polyacrylamide support has a molecular weight exclusion limit of greater than about 400,000 daltons.

12. A polyacrylamide support as defined in claim 11, wherein at least about 95% of the oligonucleotides are linked to the polyacrylamide support at the 5'-end of the oligonucleotides and the polyacrylamide support has a molecular weight exclusion limit of greater than about $2 \times 10^7$ daltons.

13. A polyacrylamide support as defined in claim 12, wherein the polyacrylamide support with attached oligonucleotides has the formula

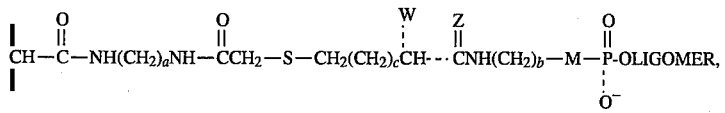

wherein

M is —NH— or oxygen;

a is 0 or 2 to 6;

b is 0 or 2 to 6 (when M is —NH—) and b is 0 to 6 (when M is —O—);

c is 1;

W is hydrogen or —NHC(=O)—R' where R' is an alkyl group having 1 to 6 carbon atoms; and Z is oxygen.

14. A polyacrylamide support as defined in claim 12, wherein the polyacrylamide support with attached oligonucleotides has the formula

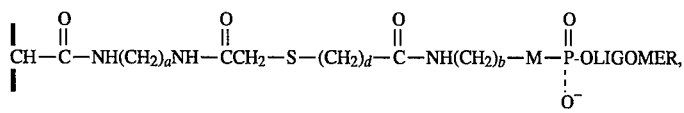

wherein

M is —NH— or oxygen;

a is 0 or 2 to 6;

b is 0 or 2 to 6 (when M is —NH—) and b is 0 to 6 (when M is —O—); and d is 2 to 6.

15. A polyacrylamide support as defined in claim 12, wherein the polyacrylamide support with attached oligonucleotides has the formula

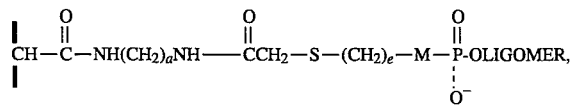

wherein

M is —NH— or oxygen;

a is 0 or 2 to 6; and e is 2 to 6.

16. A polyacrylamide support as defined in claim 12, wherein the polyacrylamide support with attached oligonucleotides has the formula

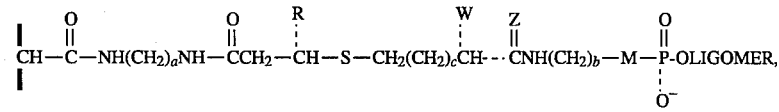

wherein

M is —NH— or oxygen;

R is hydrogen or an alkyl group containing 1 to 6 carbon atoms;

a is 0 or 2 to 6;

b is 0 or 2 to 6 (when M is —NH—) and b is 0 to 6 (when M is —O—);

c is 1;

W is hydrogen or —NHC(=O)—R' where R' is an alkyl group having 1 to 6 carbon atoms; and Z is oxygen.

17. A polyacrylamide support as defined in claim 12, wherein the polyacrylamide support with attached oligonucleotides has the formula

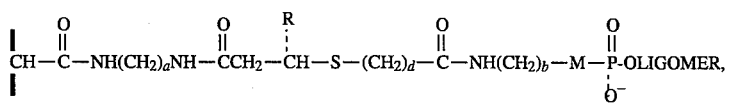

wherein

M is —NH— or oxygen;

R is hydrogen or an alkyl group containing 1 to 6 carbon atoms;

a is 0 or 2 to 6;

b is 0 or 2 to 6 (when M is —NH—) and b is 0 to 6 (when M is —O—); and d is 2 to 6.

18. A polyacrylamide support as defined in claim 12, wherein the polyacrylamide support with attached oligonucleotides has the formula

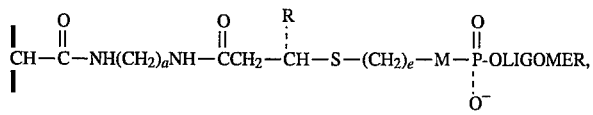

wherein
M is —NH— or oxygen;
R is hydrogen or an alkyl group containing 1 to 6 carbon atoms;
a is 0 or 2 to 6; and
e is 2 to 6.

19. A polyacrylamide support as defined in claim 12, wherein the polyacrylamide support with attached oligonucleotides has the formula

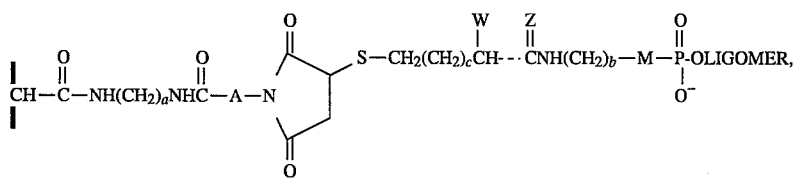

wherein
M is —NH— or oxygen;
a is 0 or 2 to 6;
b is 0 or 2 to 6 when M is —NH— or b is 0 to 6 when M is —O—;
c is 1;
A is a linking group selected from the group consisting of —(CHR)$_m$—, —C$_6$H$_4$—, —C$_6$H$_{10}$—, —(CHR)$_m$C$_6$H$_{10}$—, and —C$_6$H$_{10}$(CHR)$_m$— where m is an integer equal to 1 to 6 and R is hydrogen or an alkyl group containing 1 to 6 carbon atoms;
W is hydrogen or —NHC(=O)—R' where R' is an alkyl group having 1 to 6 carbon atoms; and
Z is oxygen.

20. A polyacrylamide support as defined in claim 12, wherein the polyacrylamide support with attached oligonucleotides has the formula

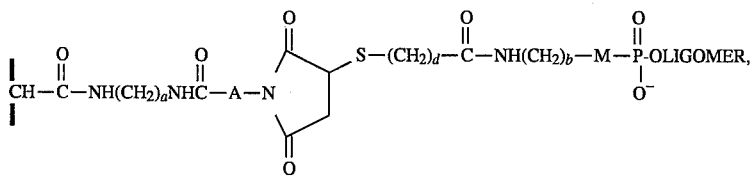

wherein
M is —NH— or oxygen;
a is 0 or 2 to 6;
b is 0 or 2 to 6 when M is —NH— or b is 0 to 6 (when M is —O—);
d is 2 to 6; and A is a linking group selected from the group consisting of —(CHR)$_m$—, —C$_6$H$_4$—, —C$_6$H$_{10}$—, —(CHR)$_m$C$_6$H$_{10}$—, and —C$_6$H$_{10}$(CHR)$_m$— where m is an integer equal to 1 to 6 and R is hydrogen or an alkyl group containing 1 to 6 carbon atoms.

21. A polyacrylamide support as defined in claim 12, wherein the polyacrylamide support with attached oligonucleotides has the formula

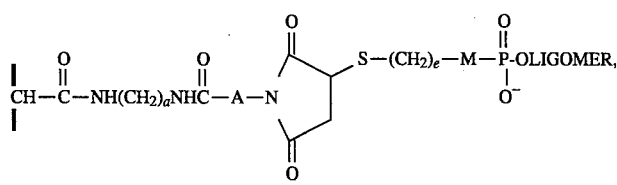

wherein

M is —NH— or oxygen;

a is 0 or 2 to 6;

e is 2 to 6; and

A is a linking group selected from —(CHR)$_m$—, —C$_6$H$_4$—, —C$_6$H$_{10}$—, —(CHR)$_m$C$_6$H$_{10}$—, or —C$_6$H$_{10}$(CHR)$_m$— where m is an integer equal to 1 to 6 and R is hydrogen or an alkyl group containing 1 to 6 carbon atoms.

22. A process for preparation of polyacrylamide supports, comprising:

coupling thiol-derivatized oligonucleotides to polyacrylamide supports in which at least a portion of the amide groups have been converted into bromoacetyl groups prior to the coupling, wherein:

the polyacrylamide supports include repeating units with carboxamide side groups of the formula:

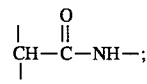

and the polyacrylamide supports have a molecular weight exclusion limit of at least about 2×10$^7$ daltons;

the coupling is effected under conditions whereby at least about 95% of attached oligonucleotides are covalently attached to the bromoacetyl groups of the support via a thioether linkage at their 5' ends;

prior to the coupling, the amide groups of the polyacrylamide supports are first modified with hydrazine and at least about 4% of the resulting hydrazide functional groups are converted into bromoacetyl groups; and at least a portion of the residual hydrazide functional groups are converted into carboxyl groups by treating the bromoacetyl-derivatized supports with an excess of a carboxylating agent.

* * * * *

UNITED STATES PATENT AND TRADEMARK OFFICE
CERTIFICATE OF CORRECTION

PATENT NO.: 5,478,893            Page 1 of 6

DATED: December 26, 1995

INVENTOR(S): Ghosh et al.

It is certified that error appears in the above-identified patent and that said Letters Patent is hereby corrected as shown below:

in the EXAMPLES, EXAMPLE 4, column 36, line 39, between "with" and "these", delete "20.";

in the EXAMPLES, TABLE VII, column 36, line 43, between "OF" and "SUPPORTS", change "TRIOL" to —THIOL—;

in the EXAMPLES, EXAMPLE 4, column 38, line 11, before "anhydride", change "gluteric" to —glutaric—;

in the EXAMPLES, TABLE VIII, column 37, line 27, between "WITH" and "SUPPORTS", change "TRIOL" to —THIOL—;

in the EXAMPLES, TABLE X, column 40, line 48, between the line beginning "~$CO_2H$" and the line beginning "35", delete the line;

in the EXAMPLES, TABLE X, column 40, lines 50 to 53, between the line beginning "35" and the line beginning "5 10% P-300-$SCH_2CO_2H$", delete

| — | 86-31 Immobilized[1] Support | fmoles | 86-32-AP (complementary) | 86-31-AP (non-complementary) | Signal/ noise (S/N) | Average S/N | —; | in the EXAMPLES, TABLE XI, column 42, line 44, between "B." and "HIV", change "TAB" to —TAS—;

UNITED STATES PATENT AND TRADEMARK OFFICE
CERTIFICATE OF CORRECTION

PATENT NO. : 5,478,893
DATED : December 26, 1995
INVENTOR(S) : Ghosh et al.

It is certified that error appears in the above-indentified patent and that said Letters Patent is hereby corrected as shown below:

in Claim 1, column 50, line 42, after "to" change "20;" to —20 when M is -O-;—, in Claim 1, column 50, line 46, between "-(CHR)$_m$-," and "-C$_6$H$_{10}$-," change "-C$_6$H-" to — -C$_6$H$_4$- —, in Claim 4, column 50, line 65, after "polyacrylamide support", change "as defined in claim 3" to —of claim 3—, in Claim 4, column 51, lines 10 to 12, change
"wherein
    M is -NH- or oxygen;
    b is 0 or 2 to 6 (when M is -NH-) or b is 0 to 6 (when M is -O-);"
to
— M is -NH- or oxygen;
    b is 0 or 2 to 6 when M is -NH- or b is 0 to 6 when M is -O-;—

In Claim 6, column 51, line 49, after "polyacrylamide support", change "as defined in claim 3" to —of claim 3—, in Claim 6, column 51, line 60 to 66, change
"wherein
    M is -NH- or oxygen;
    a is 0 or 2 to 6;
    b is 0 or 2 to 6 when M is -NH- or b is 0 to 6 (when M is -O-);"
to
— M is -NH- or oxygen;
    a is 0 or 2 to 6;
    b is 0 or 2 to 6 when M is -NH- or b is 0 to 6 when M is -O-;—

UNITED STATES PATENT AND TRADEMARK OFFICE
CERTIFICATE OF CORRECTION

PATENT NO.: 5,478,893

DATED: December 26, 1995

INVENTOR(S): Ghosh et al.

It is certified that error appears in the above-identified patent and that said Letters Patent is hereby corrected as shown below:

IN THE CLAIMS in Claim 7, column 52, line 29, after "polyacrylamide support", change "as defined in claim 3" to —of claim 3—;

in Claim 7, column 52, lines 44 to 49, change
"wherein
    M is -NH- or oxygen;
    a is 0 or 2 to 6;
    b is 0 or 2 to 6 (when M is -NH-) or b is 0 to 6 (when M is -O-);"
to
—   M is -NH- or oxygen;
    a is 0 or 2 to 6;
    b is 0 or 2 to 6 when M is -NH- or b is 0 to 6 when M is -O-;—

In Claim 8, column 52, lines 64, after "polyacrylamide support", change "as defined in claim 3" to —of claim 3—;

In Claim 8, column 53, lines 8 to 15, change
"wherein
    M is -NH- or oxygen;
    R is hydrogen or an alkyl group containing 1 to 6 carbon atoms;
    a is 0 or 2 to 6;
    b is 0 or 2 to 6 (when M is -NH-) and b is 0 to 6 (when M is -O-); and"
to
—   M is -NH- or oxygen;
    R is hydrogen or an alkyl group containing 1 to 6 carbon atoms;
    a is 0 or 2 to 6;
    b is 0 or 2 to 6 when M is -NH- or b is 0 to 6 when M is -O-; and—

UNITED STATES PATENT AND TRADEMARK OFFICE
CERTIFICATE OF CORRECTION

PATENT NO.: 5,478,893

DATED: December 26, 1995

INVENTOR(S): Ghosh et al.

It is certified that error appears in the above-identified patent and that said Letters Patent is hereby corrected as shown below:

IN THE CLAIMS in Claim 13, column 56, line 45, after "polyacrylamide support", change "as defined in claim 12" to —of claim 12—;

in Claim 13, column 56, lines 57 to 62, change
"wherein
　M is -NH- or oxygen;
　a is 0 or 2 to 6;
　b is 0 or 2 to 6 (when M is -NH-) and b is 0 to 6 (when M is -O-);"
to
— M is -NH- or oxygen;
　a is 0 or 2 to 6;
　b is 0 or 2 to 6 when M is -NH- or b is 0 to 6 when M is -O-; — in Claim 14, column 57, line 1, after "polyacrylamide support", change "as defined in claim 12" to —of claim 12—;

in Claim 14, column 57, lines 13 to 17, change
"wherein
　M is -NH- or oxygen;
　a is 0 or 2 to 6;
　b is 0 or 2 to 6 (when M is -NH-) and b is 0 to 6 (when M is -O-); and"
to
— M is -NH- or oxygen;
　a is 0 or 2 to 6;
　b is 0 or 2 to 6 when M is -NH- or b is 0 to 6 when M is -O-; and— in Claim 16, column 57, line 35, after "polyacrylamide support", change "as defined in claim 12" to —of claim 12—;

UNITED STATES PATENT AND TRADEMARK OFFICE
CERTIFICATE OF CORRECTION

PATENT NO.: 5,478,893

DATED: December 26, 1995

INVENTOR(S): Ghosh et al.

It is certified that error appears in the above-identified patent and that said Letters Patent is hereby corrected as shown below:

IN THE CLAIMS in Claim 16, column 57, lines 45 to 61, change
"wherein
    M is -NH- or oxygen;
    R is hydrogen or an alkyl group containing 1 to 6 carbon atoms;
    a is 0 or 2 to 6;
    b is 0 or 2 to 6 (when M is -NH-) and b is 0 to 6 (when M is -O-);"
to
—     M is -NH- or oxygen;
    a is 0 or 2 to 6;
    R is hydrogen or an alkyl group containing 1 to 6 carbon atoms;
    b is 0 or 2 to 6 when M is -NH- or b is 0 to 6 when M is -O-; — in Claim 17, column 58, line 1, after "polyacrylamide support", change "as defined in claim 12" to —of claim 12—;

in Claim 17, column 58, lines 56 to 63, change
"wherein
    M is -NH- or oxygen;
    R is hydrogen or an alkyl group containing 1 to 6 carbon atoms;
    a is 0 or 2 to 6;
    b is 0 or 2 to 6 (when M is -NH-) and b is 0 to 6 (when M is -O-); and"
to
—     M is -NH- or oxygen;
    R is hydrogen or an alkyl group containing 1 to 6 carbon atoms;
    a is 0 or 2 to 6;
    b is 0 or 2 to 6 when M is -NH- or b is 0 to 6 when M is -O-; and—

UNITED STATES PATENT AND TRADEMARK OFFICE
CERTIFICATE OF CORRECTION

PATENT NO.: 5,478,893

DATED: December 26, 1995

INVENTOR(S): Ghosh et al.

It is certified that error appears in the above-identified patent and that said Letters Patent is hereby corrected as shown below:

IN THE CLAIMS (continued):

in Claim 20, column 59, line 45, after "polyacrylamide support", change "as defined in claim 12" to —of claim 12—; and in Claim 20, column 59, lines 60 to 65, change "wherein
M is -NH- or oxygen;
a is 0 or 2 to 6;
b is 0 or 2 to 6 (when M is -NH-) and b is 0 to 6 (when M is -O-);"
to
— M is -NH- or oxygen;
a is 0 or 2 to 6;
b is 0 or 2 to 6 when M is -NH- or b is 0 to 6 when M is -O-; —.

Signed and Sealed this

Eighteenth Day of June, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,478,893  Page 1 of 2
DATED : December 26, 1995
INVENTOR(S) : Ghosh, et al It is certified that error appears in the above-indentified patent and that said Letters Patent is hereby corrected as shown below:

IN THE CLAIMS:

in claim 2, column 50, line 53, replace "as defined in" with —of—;
in claim 3, column 50, line 59, replace "as defined in" with —of—;
in claim 5, column 51, line 17, replace "as defined in" with —of—;
in claim 5, column 51, lines 29 to 44, replace
"wherein
M is -NH- or oxygen;
R is hydrogen or an alkyl group containing 1 to 6 carbon atoms;
a is 0 or 2 to 6;
b is 0 or 2 to 6 (when M is -NH-) and b is 0 to 6 (when M is -O-);"
with
—M is -NH- or oxygen;
R is hydrogen or an alkyl group containing 1 to 6 carbon atoms;
a is 0 or 2 to 6;
b is 0 or 2 to 6 when M is -NH- or b is 0 to 6 when M is -O-;—;
in claim 9, column 53, line 17, replace "as defined in" with —of—;
in claim 10, column 55, in the third chemical structure from the top, change "$CH_2)_a$" to —$(CH_2)_a$—;

UNITED STATES PATENT AND TRADEMARK OFFICE
CERTIFICATE OF CORRECTION

PATENT NO. : 5,478,893
DATED : December 26, 1995
INVENTOR(S) : Ghosh, et al

It is certified that error appears in the above-indentified patent and that said Letters Patent is hereby corrected as shown below:

in claim 11, column 55, line 64, replace "as defined in" with —of—;
in claim 12, column 56, line 38, replace "as defined in" with —of—;
in claim 15, column 57, line 19, replace "as defined in" with —of—;
in claim 18, column 58, line 65, replace "as defined in" with —of—; and
in claim 19, column 59, line 59, replace "as defined in" with —of—.

Signed and Sealed this

First Day of April, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:1:

GCACACAAGT AGACCCTGAA CTAGCAGACC A     31

( 2 ) INFORMATION FOR SEQ ID NO:2:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

AACCAATAAG AAGATGAGGC ATAGCAGCA     29

( 2 ) INFORMATION FOR SEQ ID NO:3:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

AGTCTAGCAG AAGAAGAGGT AGTAATTAGA     30

( 2 ) INFORMATION FOR SEQ ID NO:4:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

AGTCTAGATT GGTAATAACA ACATATT     27

( 2 ) INFORMATION FOR SEQ ID NO:5:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

AGAACTCAAG ACTTCTGGGA AGTTC     25

( 2 ) INFORMATION FOR SEQ ID NO:6:

( i ) SEQUENCE CHARACTERISTICS:
    ( A ) LENGTH: 27 base pairs
    ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

AGGATCTGAC TTAGAAATAG GGCAGCA 27

( 2 ) INFORMATION FOR SEQ ID NO:7:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

ATGGGTTATG AACTCCATCC TGATAAATGG 30

( 2 ) INFORMATION FOR SEQ ID NO:8:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

GTTCCGCCCT TCCTGAAGTG CCC 23

( 2 ) INFORMATION FOR SEQ ID NO:9:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

GTTCCGCCCT TCCTGAAGTG CCCTTATTG 29

( 2 ) INFORMATION FOR SEQ ID NO:10:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

AATTTAATAC GACTCACTAT AGGGACACCT AGGGCTAACT ATGTGTCCTA ATAAGG 56

( 2 ) INFORMATION FOR SEQ ID NO:11:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

ACACCATATG TATGTTTCAG GGAAAGCTA  29